(12) United States Patent
Matsumoto et al.

(10) Patent No.: US 11,774,447 B2
(45) Date of Patent: Oct. 3, 2023

(54) DETECTION OF CITRULLINATED INTER-ALPHA-TRYPSIN INHIBITOR HEAVY CHAIN 4 (ITIH4)

(71) Applicant: University of Tsukuba, Ibaraki (JP)

(72) Inventors: Isao Matsumoto, Ibaraki (JP); Takayuki Sumida, Ibaraki (JP); Hoshimi Kawaguchi, Ibaraki (JP)

(73) Assignee: University of Tsukuba, Ibaraki (JP)

( * ) Notice: Subject to any disclaimer, the term of this patent is extended or adjusted under 35 U.S.C. 154(b) by 677 days.

(21) Appl. No.: 16/625,972

(22) PCT Filed: Jul. 2, 2018

(86) PCT No.: PCT/JP2018/025020
§ 371 (c)(1),
(2) Date: Dec. 23, 2019

(87) PCT Pub. No.: WO2019/009231
PCT Pub. Date: Jan. 10, 2019

(65) Prior Publication Data
US 2020/0173990 A1 Jun. 4, 2020

(30) Foreign Application Priority Data

Jul. 6, 2017 (JP) .................................. 2017-132888
Jan. 16, 2018 (JP) ................................ 2018-005038

(51) Int. Cl.
*G01N 33/564* (2006.01)
*C07K 16/38* (2006.01)

(52) U.S. Cl.
CPC ........... *G01N 33/564* (2013.01); *C07K 16/38* (2013.01); *G01N 2333/811* (2013.01); *G01N 2440/18* (2013.01)

(58) Field of Classification Search
None
See application file for complete search history.

(56) References Cited

U.S. PATENT DOCUMENTS

2011/0244492 A1* 10/2011 Ossetrova .......... G01N 33/6812
435/7.92

FOREIGN PATENT DOCUMENTS

JP   2017-507337 A    3/2017
WO   2015/104563 A1   7/2015

OTHER PUBLICATIONS

Harlow et al. (Antibodies, A Laboratory Manual, Cold Spring Harbor laboratory, 1988, pp. 25-26 and 37-59 (Year: 1988).*
Edwards et al., The remarkable flexibility of the human antibody repertoire; isolation of over one thousand different antibodies to a single protein, BLyS, J. Mol. Biol. (2003) 334, 103-118, DOI: 10.1016/j.jmb.2003.09.054 (Year: 2003).*
Meyer et al. , New Insights in Type I and II CD20 Antibody Mechanisms-of-Action With a Panel of Novel CD20 Antibodies, British Journal of Haematology, 2018, 180, 808-820, |https://doi.org/10.1111/bjh.15132. (Year: 2018).*
Turunen et al., Rheumatoid arthritis antigens homocitrulline and citrulline are generated by local myeloperoxidase and peptidyl arginine deiminases 2, 3 and 4 in rheumatoid nodule and synovial tissue, Arthritis Research & Therapy, 18, (2016), (15 pages) (Year: 2016).*
Harlow et al. (Antibodies, A Laboratory Manual, Cold Spring Harbor Laboratory, 1988, pp. 48-54) (Year: 1988).*
Seward et al., Peptides Presented by HLA-DR Molecules in Synovia of Patients with Rheumatoid Arthritis or Antibiotic-Refractory Lyme Arthritis, Molecular & Cellular Proteomics, 10(3), (2011) (14 pages). (Year: 2011).*
Van Steenbergen et al., "The Preclinical Phase of Rheumatoid Arthritis: What is Acknowledged and What Needs to be Assessed?" Arthritis & Rheumatism, 65 (9): 2219-2232 (2013).
Sakkas et al., "Anti-citrullinated peptides as autoantigens in rheumatoid arthritis-relevance to treatment," Autoimmunity Reviews, 13: 1114-1120 (2014).
Umeda et al., "Anti-citrullinated glucose-6-phosphate isomerase peptide antibodies in patients with rheumatoid arthritis are associated with HLA-DRB1 shared epitope alleles and disease activity," Clinical and Experimental Immunology, 172: 44-53 (2013).
Kinloch et al., "Synovial Fluid is a Site of Citrullination of Autoantigens in Inflammatory Arthritis," Arthritis & Rheumatism, 58 (8): 2287-2295 (2008).
Van Beers et al., "The Rheumatoid Arthritis Synovial Fluid Citrullinome Reveals Novel Citrullinated Epitopes in Apolipoprotein E, Myeloid Nuclear Differentiation Antigen, and Beta-Actin," Arthritis & Rheumatism, 65 (1): 69-80 (2013).
Matsui et al., "Diagnostic Utility of Anti-Cyclic Citrullinated Peptide Antibodies for Very Early Rheumatoid Arthritis," Journal of Rheumatology, 33: (12): 2390-2397 (2006).
Kawaguchi et al., "Identification of novel biomarker as citrullinated inter-alpha-trypsin inhibitor heavy chain 4, specifically increased in sera with experimental and rheumatoid arthritis," Arthritis Research & Therapy, 20: (66): 1-13 (2018).
International Search Report issued in corresponding International Patent Application No. PCT/JP2018/025020 dated Sep. 18, 2018.

* cited by examiner

*Primary Examiner* — Ellen J Marcsisin
(74) *Attorney, Agent, or Firm* — Morgan, Lewis & Bockius LLP

(57) ABSTRACT

This invention provides a method for diagnosis of rheumatoid arthritis of a subject, a method for assisting diagnosis of rheumatoid arthritis, and a method for monitoring disease activity of rheumatoid arthritis and/or therapeutic effects of an agent for rheumatoid arthritis, comprising detecting citrullination of an arginine residue of the inter-α-trypsin inhibitor heavy chain (ITIH) 4 in a biological sample obtained from the subject. This invention also provides a citrullinated protein derived from the protein having the amino acid sequence as shown in SEQ ID NO: 1 or 5 by modification of arginine 438 into citrulline or a fragment thereof, an antibody binding to such citrullinated protein, and an agent for diagnosis of rheumatoid arthritis comprising such antibody.

11 Claims, 18 Drawing Sheets

Specification includes a Sequence Listing.

Fig. 2
A
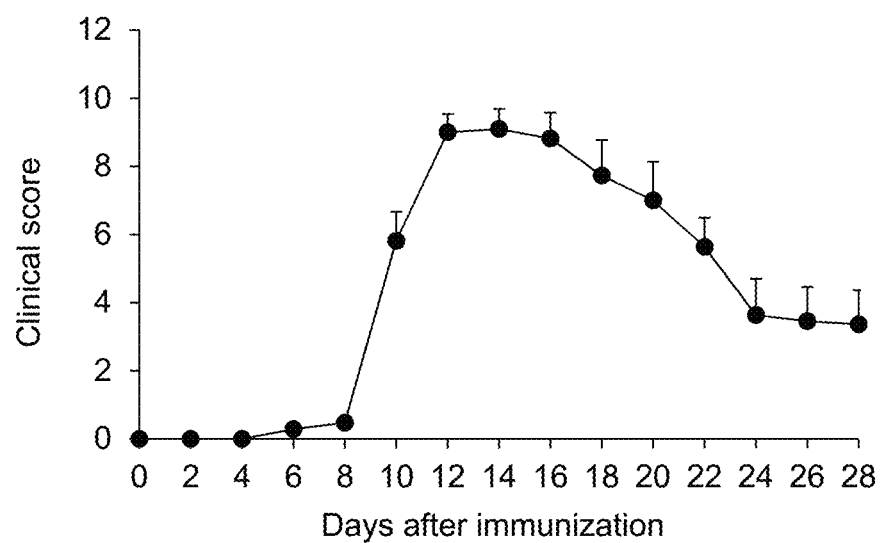
B
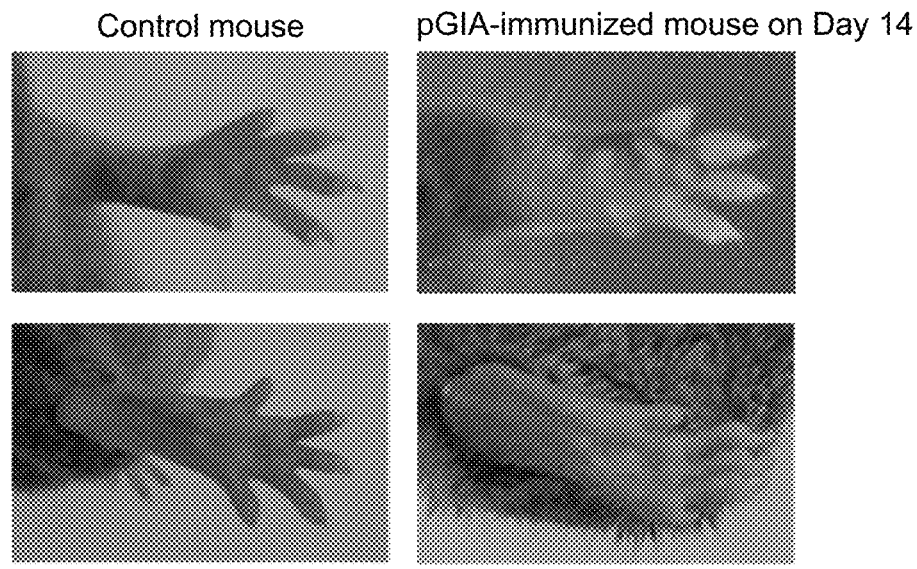
Control mouse     pGIA-immunized mouse on Day 14

Fig. 3
A
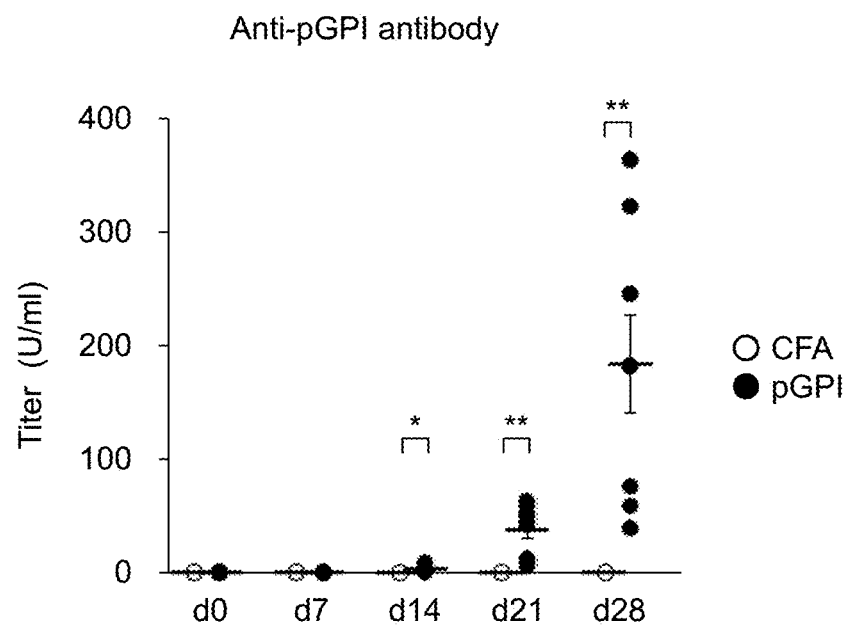
B
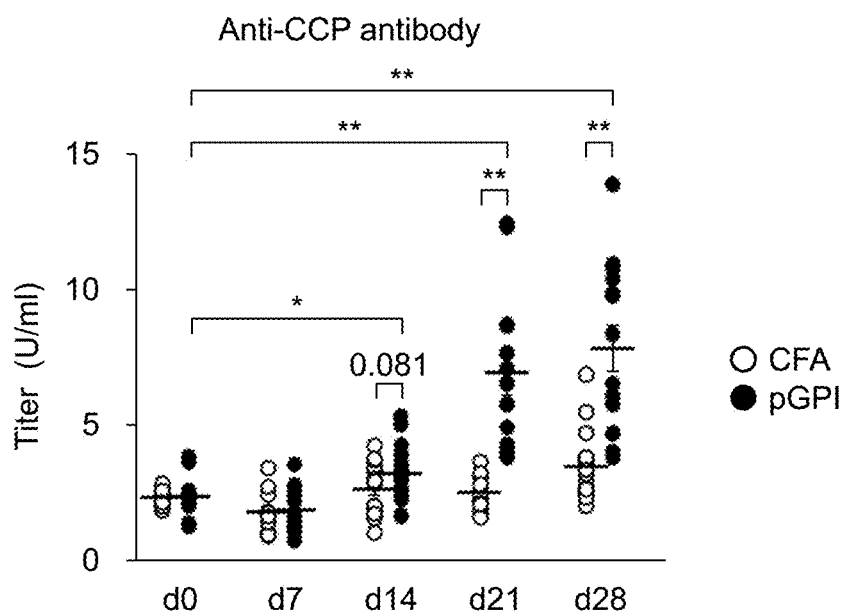

Fig. 5
A
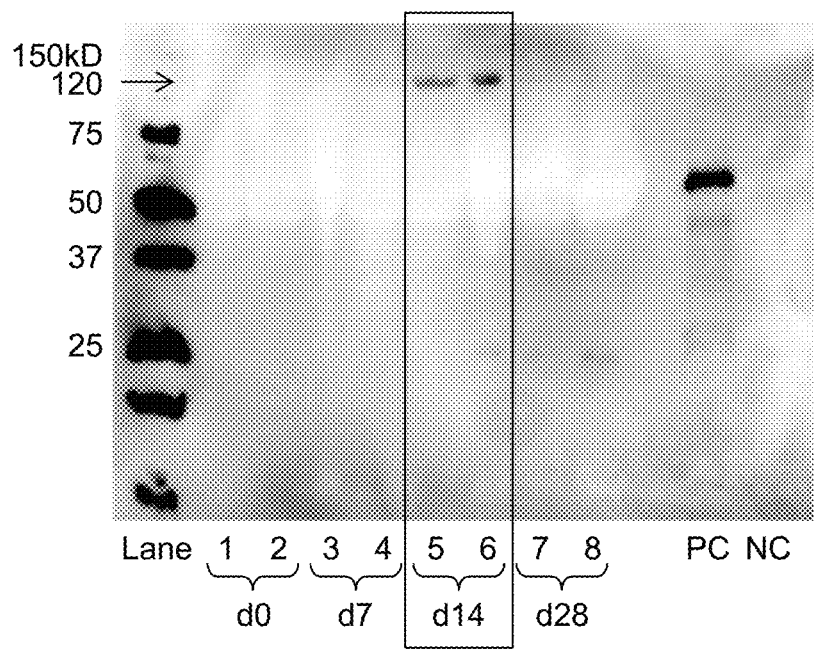
B
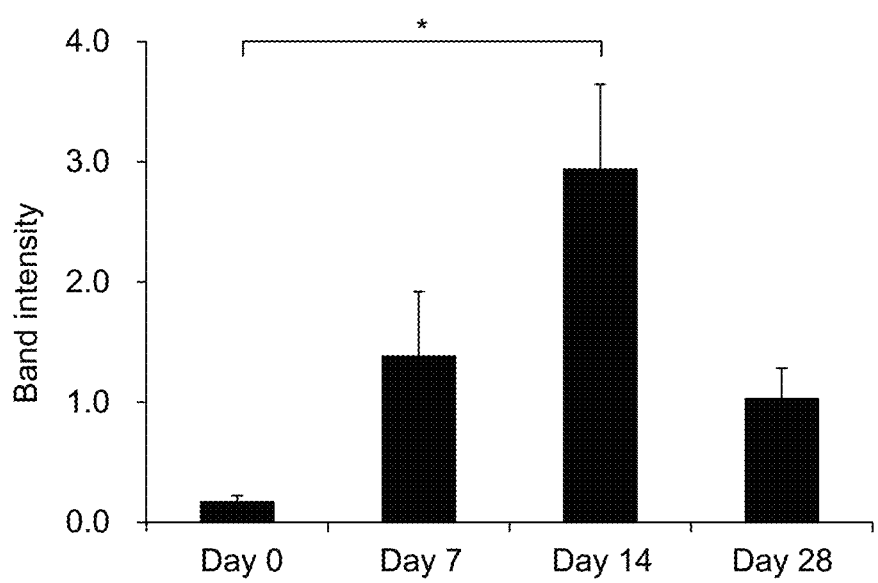

Fig. 6
A
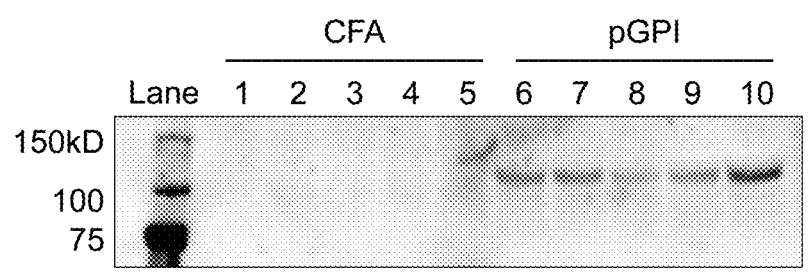
B
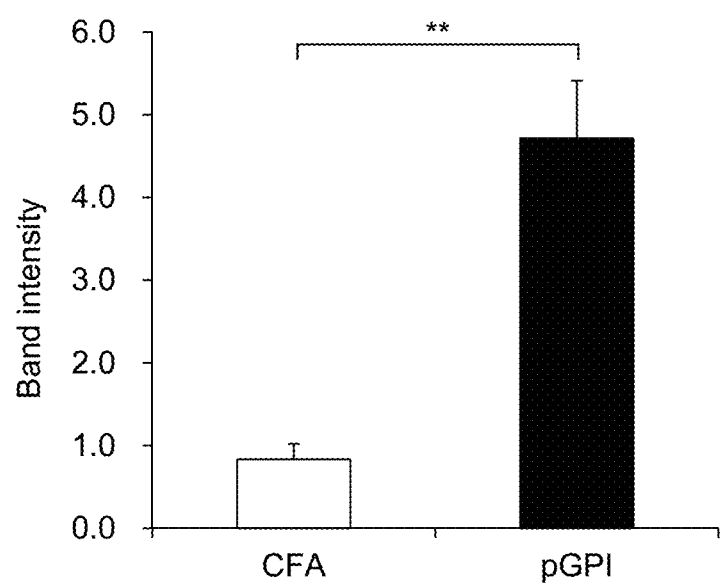

Fig. 9
A
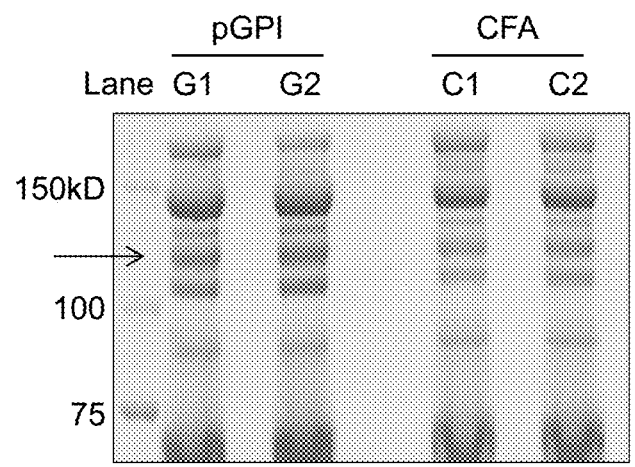
B
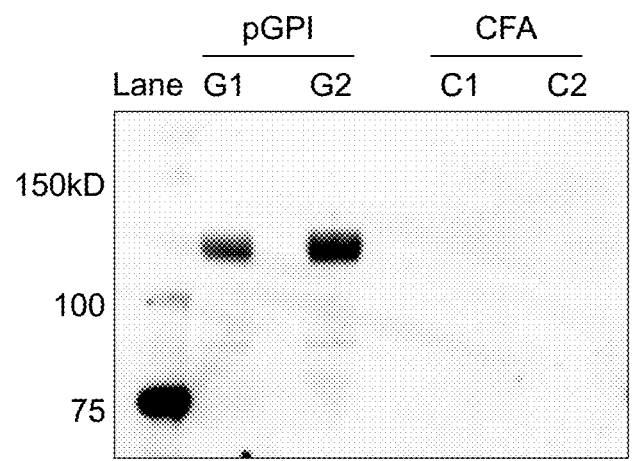

Fig. 10
A
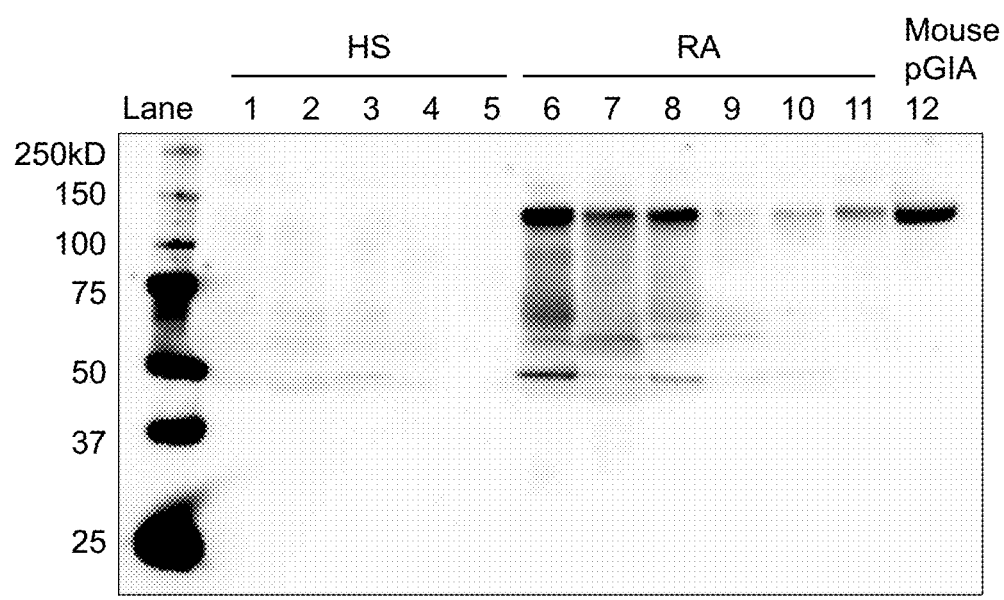
B
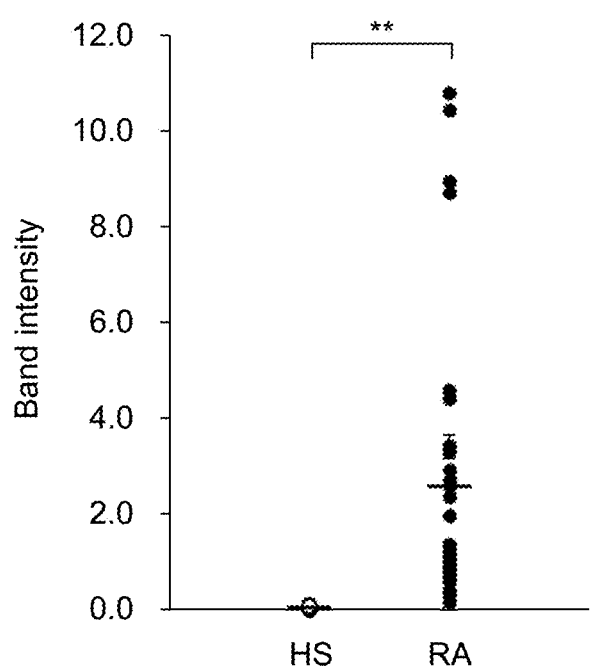

Fig. 13
A
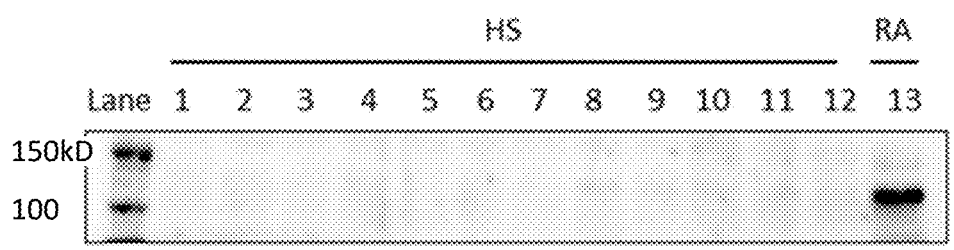
B
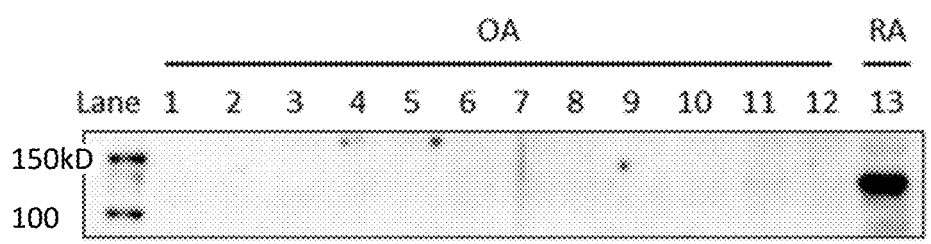
C
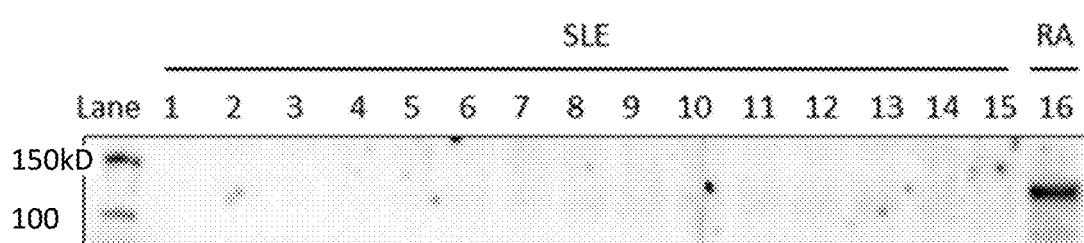
D
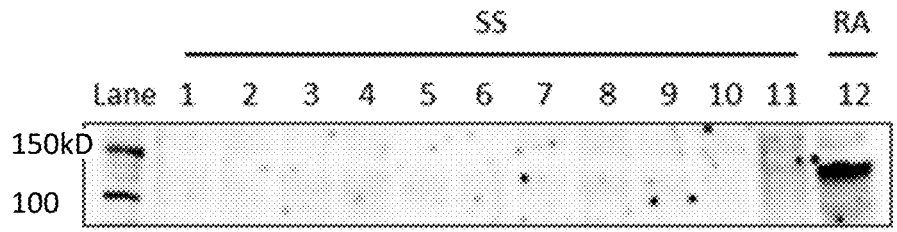
E
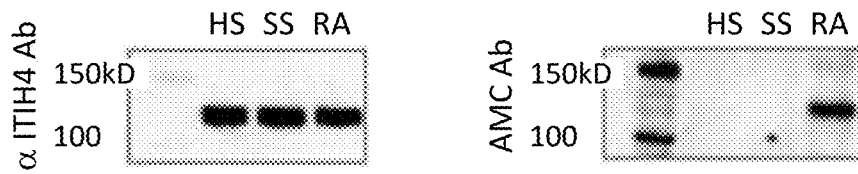

Fig. 17
A
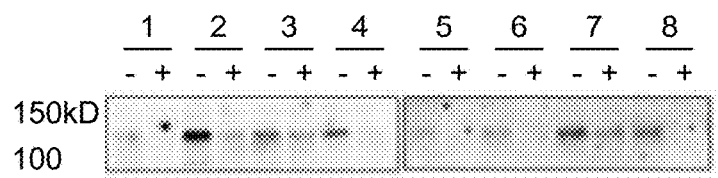
B
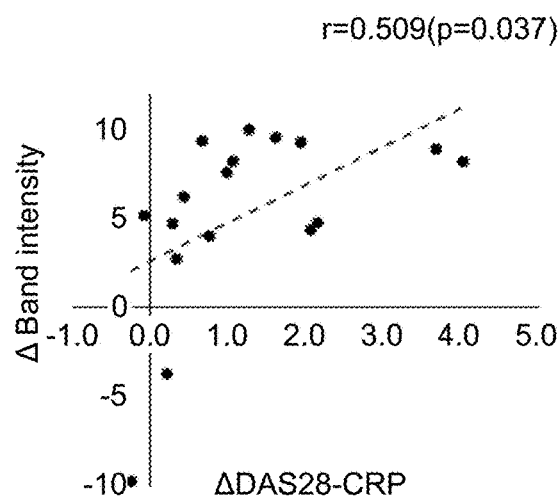
C
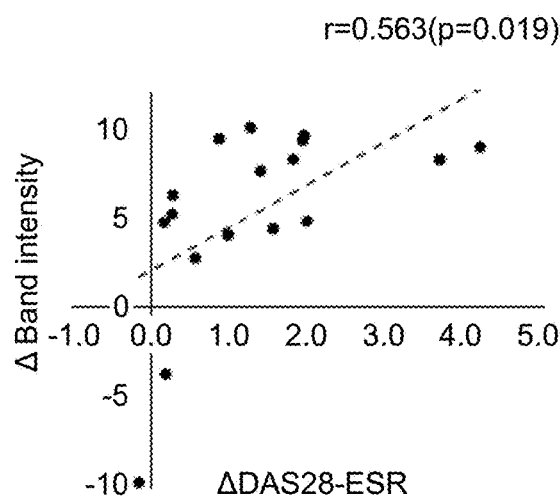

SEQUENCE LISTING

```
<160> NUMBER OF SEQ ID NOS: 8

<210> SEQ ID NO 1
<211> LENGTH: 942
<212> TYPE: PRT
<213> ORGANISM: Mus musculus

<400> SEQUENCE: 1

Met Lys Ser Pro Ala Pro Ala His Met Trp Asn Leu Val Leu Phe Leu
1               5                   10                  15

Pro Ser Leu Leu Ala Val Leu Pro Thr Thr Thr Ala Glu Lys Asn Gly
                20                  25                  30

Ile Asp Ile Tyr Ser Leu Thr Val Asp Ser Arg Val Ser Ser Arg Phe
            35                  40                  45

Ala His Thr Val Val Thr Ser Arg Val Val Asn Arg Ala Asp Ala Val
        50                  55                  60

Gln Glu Ala Thr Phe Gln Val Glu Leu Pro Arg Lys Ala Phe Ile Thr
65                  70                  75                  80
```

```
Asn Phe Ser Met Ile Ile Asp Gly Val Thr Tyr Pro Gly Val Val Lys
                85                  90                  95
Glu Lys Ala Glu Ala Gln Lys Gln Tyr Ser Ala Val Gly Arg Gly
            100                 105                 110
Glu Ser Ala Gly Ile Val Lys Thr Thr Gly Arg Gln Thr Glu Lys Phe
            115                 120                 125
Glu Val Ser Val Asn Val Ala Pro Gly Ser Lys Ile Thr Phe Glu Leu
            130                 135                 140
Ile Tyr Gln Glu Leu Leu Gln Arg Arg Leu Gly Met Tyr Glu Leu Leu
145                 150                 155                 160
Leu Lys Val Arg Pro Gln Gln Leu Val Lys His Leu Gln Met Asp Ile
                165                 170                 175
Tyr Ile Phe Glu Pro Gln Gly Ile Ser Ile Leu Glu Thr Glu Ser Thr
                180                 185                 190
Leu Met Thr Pro Glu Leu Ala Asn Ala Leu Thr Thr Ser Gln Asn Lys
            195                 200                 205
Thr Lys Ala His Ile Arg Phe Lys Pro Thr Leu Ser Gln Gln Lys
            210                 215                 220
Ser Gln Ser Glu Gln Asp Thr Val Leu Asn Gly Asp Phe Ile Val Arg
225                 230                 235                 240
Tyr Asp Val Asn Arg Ser Asp Ser Gly Gly Ser Ile Gln Ile Glu Glu
                245                 250                 255
Gly Tyr Phe Val His His Phe Ala Pro Glu Asn Leu Pro Thr Met Ser
                260                 265                 270
Lys Asn Val Ile Phe Val Ile Asp Lys Ser Gly Ser Met Ser Gly Lys
                275                 280                 285
Lys Ile Gln Gln Thr Arg Glu Ala Leu Val Lys Ile Leu Lys Asp Leu
            290                 295                 300
Ser Pro Gln Asp Gln Phe Asn Leu Ile Glu Phe Ser Gly Glu Ala Asn
305                 310                 315                 320
Gln Trp Lys Gln Ser Leu Val Gln Ala Thr Glu Glu Asn Leu Asn Lys
                325                 330                 335
Ala Val Asn Tyr Ala Ser Arg Ile Arg Ala His Gly Gly Thr Asn Ile
            340                 345                 350
Asn Asn Ala Val Leu Leu Ala Val Glu Leu Leu Asp Arg Ser Asn Gln
            355                 360                 365
Ala Glu Leu Leu Pro Ser Lys Ser Val Ser Leu Ile Ile Leu Leu Thr
            370                 375                 380
Asp Gly Asp Pro Thr Val Gly Glu Thr Asn Pro Thr Ile Ile Gln Asn
385                 390                 395                 400
Asn Val Arg Glu Ala Ile Asn Gly Gln Tyr Ser Leu Phe Cys Leu Gly
                405                 410                 415
Phe Gly Phe Asp Val Asn Tyr Pro Phe Leu Glu Lys Met Ala Leu Asp
                420                 425                 430
Asn Gly Gly Leu Ala Arg Arg Ile Tyr Glu Asp Ser Asp Ser Ala Leu
            435                 440                 445
Gln Leu Gln Asp Phe Tyr His Glu Val Ala Asn Pro Leu Leu Ser Ser
            450                 455                 460
Val Ala Phe Glu Tyr Pro Ser Asp Ala Val Glu Glu Val Thr Arg Tyr
465                 470                 475                 480
Lys Phe Gln His His Phe Lys Gly Ser Glu Met Val Val Ala Gly Lys
                485                 490                 495
```

```
Leu Gln Asp Gln Gly Pro Asp Val Leu Leu Ala Lys Val Ser Gly Gln
                500                 505                 510
Met His Met Gln Asn Ile Thr Phe Gln Thr Glu Ala Ser Val Ala Gln
        515                 520                 525
Gln Glu Lys Glu Phe Lys Ser Pro Lys Tyr Ile Phe His Asn Phe Met
    530                 535                 540
Glu Arg Leu Trp Ala Leu Leu Thr Ile Gln Gln Leu Glu Gln Arg
545                 550                 555                 560
Ile Ser Ala Ser Gly Ala Glu Leu Glu Ala Leu Glu Ala Gln Val Leu
                565                 570                 575
Asn Leu Ser Leu Lys Tyr Asn Phe Val Thr Pro Leu Thr His Met Val
            580                 585                 590
Val Thr Lys Pro Glu Gly Gln Glu Gln Phe Gln Val Ala Glu Lys Pro
        595                 600                 605
Val Glu Val Gly Asp Gly Met Gln Arg Leu Pro Leu Ala Ala Gln Ala
    610                 615                 620
His Pro Phe Arg Pro Pro Val Arg Gly Ser Lys Leu Met Thr Val Leu
625                 630                 635                 640
Lys Gly Ser Arg Ser Gln Ile Pro Arg Arg Gly Asp Ala Val Arg Ala
                645                 650                 655
Ser Arg Gln Tyr Ile Pro Pro Gly Phe Pro Gly Pro Pro Gly Pro Pro
            660                 665                 670
Gly Phe Pro Ala Pro Pro Gly Pro Pro Gly Phe Pro Ala Pro Pro Gly
        675                 680                 685
Pro Pro Leu Ala Ser Gly Ser Asp Phe Ser Leu Gln Pro Ser Tyr Glu
    690                 695                 700
Arg Met Leu Ser Leu Pro Ser Val Ala Ala Gln Tyr Pro Ala Asp Pro
705                 710                 715                 720
His Leu Val Val Thr Glu Lys Ser Lys Glu Ser Thr Ile Pro Glu Glu
                725                 730                 735
Ser Pro Asn Pro Asp His Pro Gln Val Pro Thr Ile Thr Leu Pro Leu
            740                 745                 750
Pro Gly Ser Ser Val Asp Gln Leu Cys Val Asp Ile Leu His Ser Glu
        755                 760                 765
Lys Pro Met Lys Leu Phe Val Asp Pro Ser Gln Gly Leu Glu Val Thr
    770                 775                 780
Gly Lys Tyr Glu Asn Thr Gly Phe Ser Trp Leu Glu Val Thr Ile Gln
785                 790                 795                 800
Lys Pro His Leu Gln Val His Ala Thr Pro Glu Arg Leu Val Val Thr
                805                 810                 815
Arg Gly Arg Lys Asn Thr Glu Tyr Lys Trp Lys Thr Leu Phe Ser
            820                 825                 830
Val Leu Pro Gly Leu Lys Met Thr Met Asn Met Met Gly Leu Leu Gln
        835                 840                 845
Leu Ser Gly Pro Asp Lys Val Thr Ile Gly Leu Leu Ser Leu Asp Asp
    850                 855                 860
Pro Gln Arg Gly Leu Met Leu Leu Leu Asn Asp Thr Gln His Phe Ser
865                 870                 875                 880
Asn Asn Val Lys Gly Glu Leu Gly Gln Phe Tyr Arg Asp Ile Val Trp
                885                 890                 895
Glu Pro Pro Val Glu Pro Asp Asn Thr Lys Arg Thr Val Lys Val Gln
            900                 905                 910
```

```
Gly Val Asp Tyr Leu Ala Thr Arg Glu Leu Lys Leu Ser Tyr Gln Glu
            915                 920                 925

Gly Phe Pro Gly Ala Glu Ile Ser Cys Trp Thr Val Glu Ile
    930                 935                 940

<210> SEQ ID NO 2
<211> LENGTH: 942
<212> TYPE: PRT
<213> ORGANISM: Mus musculus
<220> FEATURE:
<221> NAME/KEY: misc_feature
<222> LOCATION: (438)..(438)
<223> OTHER INFORMATION: Xaa is citrulline

<400> SEQUENCE: 2

Met Lys Ser Pro Ala Pro Ala His Met Trp Asn Leu Val Leu Phe Leu
1               5                   10                  15

Pro Ser Leu Leu Ala Val Leu Pro Thr Thr Ala Glu Lys Asn Gly
            20                  25                  30

Ile Asp Ile Tyr Ser Leu Thr Val Asp Ser Arg Val Ser Ser Arg Phe
            35                  40                  45

Ala His Thr Val Val Thr Ser Arg Val Val Asn Arg Ala Asp Ala Val
        50                  55                  60

Gln Glu Ala Thr Phe Gln Val Glu Leu Pro Arg Lys Ala Phe Ile Thr
65              70                  75                  80

Asn Phe Ser Met Ile Ile Asp Gly Val Thr Tyr Pro Gly Val Val Lys
                85                  90                  95

Glu Lys Ala Glu Ala Gln Lys Gln Tyr Ser Ala Ala Val Gly Arg Gly
            100                 105                 110

Glu Ser Ala Gly Ile Val Lys Thr Thr Gly Arg Gln Thr Glu Lys Phe
        115                 120                 125

Glu Val Ser Val Asn Val Ala Pro Gly Ser Lys Ile Thr Phe Glu Leu
    130                 135                 140

Ile Tyr Gln Glu Leu Leu Gln Arg Arg Leu Gly Met Tyr Glu Leu Leu
145                 150                 155                 160

Leu Lys Val Arg Pro Gln Gln Leu Val Lys His Leu Gln Met Asp Ile
                165                 170                 175

Tyr Ile Phe Glu Pro Gln Gly Ile Ser Ile Leu Glu Thr Glu Ser Thr
            180                 185                 190

Leu Met Thr Pro Glu Leu Ala Asn Ala Leu Thr Thr Ser Gln Asn Lys
        195                 200                 205

Thr Lys Ala His Ile Arg Phe Lys Pro Thr Leu Ser Gln Gln Gln Lys
    210                 215                 220

Ser Gln Ser Glu Gln Asp Thr Val Leu Asn Gly Asp Phe Ile Val Arg
225                 230                 235                 240

Tyr Asp Val Asn Arg Ser Asp Ser Gly Gly Ser Ile Gln Ile Glu Glu
                245                 250                 255

Gly Tyr Phe Val His His Phe Ala Pro Glu Asn Leu Pro Thr Met Ser
            260                 265                 270

Lys Asn Val Ile Phe Val Ile Asp Lys Ser Gly Ser Met Ser Gly Lys
        275                 280                 285

Lys Ile Gln Gln Thr Arg Glu Ala Leu Val Lys Ile Leu Lys Asp Leu
    290                 295                 300

Ser Pro Gln Asp Gln Phe Asn Leu Ile Glu Phe Ser Gly Glu Ala Asn
305                 310                 315                 320
```

-continued

```
Gln Trp Lys Gln Ser Leu Val Gln Ala Thr Glu Glu Asn Leu Asn Lys
                325                 330                 335
Ala Val Asn Tyr Ala Ser Arg Ile Arg Ala His Gly Gly Thr Asn Ile
            340                 345                 350
Asn Asn Ala Val Leu Leu Ala Val Glu Leu Leu Asp Arg Ser Asn Gln
        355                 360                 365
Ala Glu Leu Leu Pro Ser Lys Ser Val Ser Leu Ile Ile Leu Leu Thr
    370                 375                 380
Asp Gly Asp Pro Thr Val Gly Glu Thr Asn Pro Thr Ile Ile Gln Asn
385                 390                 395                 400
Asn Val Arg Glu Ala Ile Asn Gly Gln Tyr Ser Leu Phe Cys Leu Gly
                405                 410                 415
Phe Gly Phe Asp Val Asn Tyr Pro Phe Leu Glu Lys Met Ala Leu Asp
            420                 425                 430
Asn Gly Gly Leu Ala Xaa Arg Ile Tyr Glu Asp Ser Asp Ser Ala Leu
        435                 440                 445
Gln Leu Gln Asp Phe Tyr His Glu Val Ala Asn Pro Leu Leu Ser Ser
    450                 455                 460
Val Ala Phe Glu Tyr Pro Ser Asp Ala Val Glu Glu Val Thr Arg Tyr
465                 470                 475                 480
Lys Phe Gln His His Phe Lys Gly Ser Glu Met Val Val Ala Gly Lys
                485                 490                 495
Leu Gln Asp Gln Gly Pro Asp Val Leu Leu Ala Lys Val Ser Gly Gln
            500                 505                 510
Met His Met Gln Asn Ile Thr Phe Gln Thr Glu Ala Ser Val Ala Gln
        515                 520                 525
Gln Glu Lys Glu Phe Lys Ser Pro Lys Tyr Ile Phe His Asn Phe Met
    530                 535                 540
Glu Arg Leu Trp Ala Leu Leu Thr Ile Gln Gln Gln Leu Glu Gln Arg
545                 550                 555                 560
Ile Ser Ala Ser Gly Ala Glu Leu Glu Ala Leu Glu Ala Gln Val Leu
                565                 570                 575
Asn Leu Ser Leu Lys Tyr Asn Phe Val Thr Pro Leu Thr His Met Val
            580                 585                 590
Val Thr Lys Pro Glu Gly Gln Glu Gln Phe Gln Val Ala Glu Lys Pro
        595                 600                 605
Val Glu Val Gly Asp Gly Met Gln Arg Leu Pro Leu Ala Ala Gln Ala
    610                 615                 620
His Pro Phe Arg Pro Pro Val Arg Gly Ser Lys Leu Met Thr Val Leu
625                 630                 635                 640
Lys Gly Ser Arg Ser Gln Ile Pro Arg Gly Asp Ala Val Arg Ala
                645                 650                 655
Ser Arg Gln Tyr Ile Pro Pro Gly Phe Pro Gly Pro Pro Gly Pro Pro
            660                 665                 670
Gly Phe Pro Ala Pro Gly Pro Pro Gly Phe Pro Ala Pro Pro Gly
        675                 680                 685
Pro Pro Leu Ala Ser Gly Ser Asp Phe Ser Leu Gln Pro Ser Tyr Glu
    690                 695                 700
Arg Met Leu Ser Leu Pro Ser Val Ala Ala Gln Tyr Pro Ala Asp Pro
705                 710                 715                 720
His Leu Val Val Thr Glu Lys Ser Lys Glu Ser Thr Ile Pro Glu Glu
                725                 730                 735
```

```
Ser Pro Asn Pro Asp His Pro Gln Val Pro Thr Ile Thr Leu Pro Leu
            740                 745                 750

Pro Gly Ser Ser Val Asp Gln Leu Cys Val Asp Ile Leu His Ser Glu
        755                 760                 765

Lys Pro Met Lys Leu Phe Val Asp Pro Ser Gln Gly Leu Glu Val Thr
    770                 775                 780

Gly Lys Tyr Glu Asn Thr Gly Phe Ser Trp Leu Glu Val Thr Ile Gln
785                 790                 795                 800

Lys Pro His Leu Gln Val His Ala Thr Pro Glu Arg Leu Val Val Thr
                805                 810                 815

Arg Gly Arg Lys Asn Thr Glu Tyr Lys Trp Lys Lys Thr Leu Phe Ser
            820                 825                 830

Val Leu Pro Gly Leu Lys Met Thr Met Asn Met Met Gly Leu Leu Gln
        835                 840                 845

Leu Ser Gly Pro Asp Lys Val Thr Ile Gly Leu Leu Ser Leu Asp Asp
    850                 855                 860

Pro Gln Arg Gly Leu Met Leu Leu Asn Asp Thr Gln His Phe Ser
865                 870                 875                 880

Asn Asn Val Lys Gly Glu Leu Gly Gln Phe Tyr Arg Asp Ile Val Trp
                885                 890                 895

Glu Pro Pro Val Glu Pro Asp Asn Thr Lys Arg Thr Val Lys Val Gln
            900                 905                 910

Gly Val Asp Tyr Leu Ala Thr Arg Glu Leu Lys Leu Ser Tyr Gln Glu
        915                 920                 925

Gly Phe Pro Gly Ala Glu Ile Ser Cys Trp Thr Val Glu Ile
    930                 935                 940

<210> SEQ ID NO 3
<211> LENGTH: 10
<212> TYPE: PRT
<213> ORGANISM: Mus musculus

<400> SEQUENCE: 3

Met Ala Leu Asp Asn Gly Gly Leu Ala Arg
1               5                   10

<210> SEQ ID NO 4
<211> LENGTH: 10
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa is citrulline

<400> SEQUENCE: 4

Met Ala Leu Asp Asn Gly Gly Leu Ala Xaa
1               5                   10

<210> SEQ ID NO 5
<211> LENGTH: 930
<212> TYPE: PRT
<213> ORGANISM: Homo sapiens

<400> SEQUENCE: 5

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30
```

```
Ile Asp Ile Tyr Ser Leu Thr Val Asp Ser Arg Val Ser Arg Phe
         35                  40                  45

Ala His Thr Val Val Thr Ser Arg Val Val Asn Arg Ala Asn Thr Val
 50                  55                  60

Gln Glu Ala Thr Phe Gln Met Glu Leu Pro Lys Lys Ala Phe Ile Thr
 65                  70                  75                  80

Asn Phe Ser Met Ile Ile Asp Gly Met Thr Tyr Pro Gly Ile Ile Lys
                 85                  90                  95

Glu Lys Ala Glu Ala Gln Ala Gln Tyr Ser Ala Ala Val Ala Lys Gly
                100                 105                 110

Lys Ser Ala Gly Leu Val Lys Ala Thr Gly Arg Asn Met Glu Gln Phe
            115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
    195                 200                 205

Thr Lys Ala His Ile Arg Phe Lys Pro Thr Leu Ser Gln Gln Gln Lys
210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
    275                 280                 285

Lys Ile Gln Gln Thr Arg Glu Ala Leu Ile Lys Ile Leu Asp Asp Leu
290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
    355                 360                 365

Glu Glu Arg Leu Pro Glu Gly Ser Val Ser Leu Ile Ile Leu Leu Thr
370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
    435                 440                 445
```

-continued

```
Gln Leu Gln Asp Phe Tyr Gln Glu Val Ala Asn Pro Leu Leu Thr Ala
    450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
        515                 520                 525

Gln Glu Ala Glu Phe Gln Ser Pro Lys Tyr Ile Phe His Asn Phe Met
530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
                580                 585                 590

Val Thr Lys Pro Asp Asp Gln Glu Gln Ser Gln Val Ala Glu Lys Pro
        595                 600                 605

Met Glu Gly Glu Ser Arg Asn Arg Asn Val His Ser Gly Ser Thr Phe
610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
                660                 665                 670

Pro Gly Pro Pro Asp Val Pro Asp His Ala Ala Tyr His Pro Phe Arg
        675                 680                 685

Arg Leu Ala Ile Leu Pro Ala Ser Ala Pro Ala Thr Ser Asn Pro
690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
        770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Leu Arg Asp Thr
850                 855                 860
```

```
Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
            885                 890                 895

Leu Arg Val Gln Gly Asn Asp His Ser Ala Thr Arg Glu Arg Arg Leu
        900                 905                 910

Asp Tyr Gln Glu Gly Pro Pro Gly Val Glu Ile Ser Cys Trp Ser Val
    915                 920                 925

Glu Leu
    930

<210> SEQ ID NO 6
<211> LENGTH: 930
<212> TYPE: PRT
<213> ORGANISM: Homo sapiens
<220> FEATURE:
<221> NAME/KEY: misc_feature
<222> LOCATION: (438)..(438)
<223> OTHER INFORMATION: Xaa is citrulline

<400> SEQUENCE: 6

Met Lys Pro Pro Arg Pro Val Arg Thr Cys Ser Lys Val Leu Val Leu
1               5                   10                  15

Leu Ser Leu Leu Ala Ile His Gln Thr Thr Ala Glu Lys Asn Gly
            20                  25                  30

Ile Asp Ile Tyr Ser Leu Thr Val Asp Ser Arg Val Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Ile Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270
```

```
Lys Asn Val Val Phe Val Ile Asp Lys Ser Gly Ser Met Ser Gly Arg
                275                 280                 285
Lys Ile Gln Gln Thr Arg Glu Ala Leu Ile Lys Ile Leu Asp Asp Leu
    290                 295                 300
Ser Pro Arg Asp Gln Phe Asn Leu Ile Val Phe Ser Thr Glu Ala Thr
305                 310                 315                 320
Gln Trp Arg Pro Ser Leu Val Pro Ala Ser Ala Glu Asn Val Asn Lys
                325                 330                 335
Ala Arg Ser Phe Ala Ala Gly Ile Gln Ala Leu Gly Gly Thr Asn Ile
                340                 345                 350
Asn Asp Ala Met Leu Met Ala Val Gln Leu Leu Asp Ser Ser Asn Gln
                355                 360                 365
Glu Glu Arg Leu Pro Glu Gly Ser Val Ser Leu Ile Ile Leu Leu Thr
            370                 375                 380
Asp Gly Asp Pro Thr Val Gly Glu Thr Asn Pro Arg Ser Ile Gln Asn
385                 390                 395                 400
Asn Val Arg Glu Ala Val Ser Gly Arg Tyr Ser Leu Phe Cys Leu Gly
                405                 410                 415
Phe Gly Phe Asp Val Ser Tyr Ala Phe Leu Glu Lys Leu Ala Leu Asp
                420                 425                 430
Asn Gly Gly Leu Ala Xaa Arg Ile His Glu Asp Ser Asp Ser Ala Leu
                435                 440                 445
Gln Leu Gln Asp Phe Tyr Gln Glu Val Ala Asn Pro Leu Leu Thr Ala
            450                 455                 460
Val Thr Phe Glu Tyr Pro Ser Asn Ala Val Glu Val Thr Gln Asn
465                 470                 475                 480
Asn Phe Arg Leu Leu Phe Lys Gly Ser Glu Met Val Val Ala Gly Lys
                485                 490                 495
Leu Gln Asp Arg Gly Pro Asp Val Leu Thr Ala Thr Val Ser Gly Lys
            500                 505                 510
Leu Pro Thr Gln Asn Ile Thr Phe Gln Thr Glu Ser Ser Val Ala Glu
            515                 520                 525
Gln Glu Ala Glu Phe Gln Ser Pro Lys Tyr Ile Phe His Asn Phe Met
            530                 535                 540
Glu Arg Leu Trp Ala Tyr Leu Thr Ile Gln Gln Leu Leu Glu Gln Thr
545                 550                 555                 560
Val Ser Ala Ser Asp Ala Asp Gln Gln Ala Leu Arg Asn Gln Ala Leu
                565                 570                 575
Asn Leu Ser Leu Ala Tyr Ser Phe Val Thr Pro Leu Thr Ser Met Val
            580                 585                 590
Val Thr Lys Pro Asp Asp Gln Glu Gln Ser Gln Val Ala Glu Lys Pro
            595                 600                 605
Met Glu Gly Glu Ser Arg Asn Arg Asn Val His Ser Gly Ser Thr Phe
            610                 615                 620
Phe Lys Tyr Tyr Leu Gln Gly Ala Lys Ile Pro Lys Pro Glu Ala Ser
625                 630                 635                 640
Phe Ser Pro Arg Arg Gly Trp Asn Arg Gln Ala Gly Ala Ala Gly Ser
                645                 650                 655
Arg Met Asn Phe Arg Pro Gly Val Leu Ser Ser Arg Gln Leu Gly Leu
                660                 665                 670
Pro Gly Pro Pro Asp Val Pro Asp His Ala Ala Tyr His Pro Phe Arg
            675                 680                 685
```

-continued

```
Arg Leu Ala Ile Leu Pro Ala Ser Ala Pro Pro Ala Thr Ser Asn Pro
    690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
770                 775                 780

Val Thr Phe Lys Asn Pro Leu Val Trp Val His Ala Ser Pro Glu His
785                 790                 795                 800

Val Val Val Thr Arg Asn Arg Ser Ser Ala Tyr Lys Trp Lys Glu
                805                 810                 815

Thr Leu Phe Ser Val Met Pro Gly Leu Lys Met Thr Met Asp Lys Thr
                820                 825                 830

Gly Leu Leu Leu Leu Ser Asp Pro Asp Lys Val Thr Ile Gly Leu Leu
            835                 840                 845

Phe Trp Asp Gly Arg Gly Glu Gly Leu Arg Leu Leu Arg Asp Thr
850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Gly Arg Arg Thr
                885                 890                 895

Leu Arg Val Gln Gly Asn Asp His Ser Ala Thr Arg Glu Arg Leu
                900                 905                 910

Asp Tyr Gln Glu Gly Pro Pro Gly Val Glu Ile Ser Cys Trp Ser Val
        915                 920                 925

Glu Leu
    930

<210> SEQ ID NO 7
<211> LENGTH: 10
<212> TYPE: PRT
<213> ORGANISM: Homo sapiens

<400> SEQUENCE: 7

Leu Ala Leu Asp Asn Gly Gly Leu Ala Arg
1               5                   10

<210> SEQ ID NO 8
<211> LENGTH: 10
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa is citrulline

<400> SEQUENCE: 8

Leu Ala Leu Asp Asn Gly Gly Leu Ala Xaa
1               5                   10
```

DETECTION OF CITRULLINATED INTER-ALPHA-TRYPSIN INHIBITOR HEAVY CHAIN 4 (ITIH4)

SEQUENCE LISTING SUBMISSION VIA EFS-WEB

A computer readable text file, entitled "SequenceListing.txt" created on or about Dec. 23, 2019 with a file size of about 33 kb contains the sequence listing for this application and is hereby incorporated by reference in its entirety.

TECHNICAL FIELD

The present invention relates to a novel agent for diagnosis of rheumatoid arthritis and a novel method for diagnosis of rheumatoid arthritis. More specifically, the present invention relates to a method for assisting diagnosis of rheumatoid arthritis of a subject comprising detecting citrullination of an arginine residue of the inter-α-trypsin inhibitor heavy chain (ITIH) 4 in a biological sample derived from the subject. Also, the present invention relates to a novel protein resulting from citrullination of a particular arginine residue of human ITIH4.

BACKGROUND ART

Rheumatoid arthritis (RA) is an inflammatory autoimmune disease that causes swelling and pain at joints and leads to deformed and fractured joints. RA is diagnosed based on comprehensive analyses of, for example, swelling and pain at joints, occurrence of inflammatory reactions, the duration of arthritis, and blood test scores described below. However, the presence of a long-term preclinical phase prior to a diagnosis of arthritis is known, and RA onset is reported to be associated with genetic risk factors and environmental risk factors (Non-Patent Document 1).

It is known that anti-citrullinated protein antibodies (ACPA) binding to citrullinated peptides are present in an RA patient's body (Non-Patent Document 2). In addition, it is suggested that a plurality of types of citrullinated proteins have increased at the joints of an RA patient and such increase may be associated with RA (Non-Patent Documents 3 to 5).

However, major citrullinated proteins in the serum and the correlation of such citrullinated proteins with the cause of a disease are not yet elucidated.

As treatment of RA, for example, drug therapy for inflammations and pains, surgical operation, and rehabilitation have been performed. In recent years, a case of clinical remission achieved by performing anti-cytokine therapy at an early stage was reported. Accordingly, an early diagnosis and an early treatment are considered necessary.

As comprehensive indices of clinical symptoms of RA, for example, Disease Activity Score (DAS) 28 that evaluates 28 joints is extensively employed. DAS28-CRP of DAS28 detects the C-reactive protein (CRP) as an inflammation marker in the blood. In addition, the blood test scores indicating rheumatoid factors and ACPA are used for RA diagnosis, and detection of ACPA is considered more accurate compared with detection of rheumatoid factors (Non-Patent Document 6).

PRIOR ART DOCUMENTS

[Non-Patent Documents]
[Non-Patent Document 1] Arthritis Rheum., 2013; 65: 2219-32
[Non-Patent Document 2] Autoimmun. Rev., 2014; 13: 1114-20
[Non-Patent Document 3] Clin. Exp. Immunol., 2013; 172: 44-53
[Non-Patent Document 4] Arthritis Rheum., 2008; 58: 2287-95
[Non-Patent Document 5] Arthritis Rheum., 2013; 65: 69-80
[Non-Patent Document 6] J. Rheumatol., 2006; 33: 2390-7

SUMMARY OF THE INVENTION

Problems to be Solved by the Invention

At present, ACPA is considered to be a useful marker for RA diagnosis since it is capable of stratification of patients with RA and patients with diseases other than RA at an early stage, and a kit used for detecting ACPA in patients is commercially available. A kit used for detecting ACPA comprises a synthetic polypeptide comprising a plurality of citrullinated peptides used as antigens ligated to each other (i.e., cyclic citrullinated peptides, CCP). Accordingly, ACPA thus detected is also referred to as an anti-CCP antibody in the art. Sensitivity of RA diagnosis with the use of the anti-CCP antibody is considered to be 76% and specificity thereof is considered to be 96% (MESACUP-2 test CCP; Scellkens G A, et al., J. Clin. Invest., 1998, 101: 273-81); however, CCP is different from the citrullinated protein that can be present in a human body.

A citrullinated protein in the serum that is associated with RA onset has not yet been identified. Accordingly, the correlation of the test results with the disease progression and the etiological significance thereof are not yet elucidated. In addition, since ACPA measurement assays autoantibodies in the patient's body, such measurement can be performed only once, and it cannot be performed for monitoring symptoms, for example.

FIG. 1 shows the results reported by J. Sokolove et al. (PLoS ONE, Vol. 7, Issue 5, e35296, 2012), which were obtained by detecting the presence of ACPA in the serum samples obtained from the subjects (the United States Armed Forces personnel) before and after disease onset (diagnosis) who had been diagnosed to have RA on the basis of clinical findings with the use of 16 types of citrullinated peptides as antigens and determining as to positivity based on the preset cut-off value. The results demonstrate that antibodies against various citrullinated peptides (ACPA subtypes) have been present in the serum since before RA onset, the amount thereof gradually increases, the abundance thereof substantially reaches the peak at the time of RA diagnosis ("0" on the horizontal axis), and then abundance reaches a plateau.

As described above, the ACPA level that had once elevated would not lower even if the symptoms are alleviated by treatment. Thus, it is not suitable as the disease activity index.

Accordingly, a novel agent for diagnosis of rheumatoid arthritis that is RA patient-specific and highly correlated with disease activity has been awaited.

Means for Solving the Problems

The present inventors had thoroughly examined as to a type of a citrullinated protein that is present in RA mouse models; i.e., mouse models of peptide glucose-6-phosphate isomerase (pGPI)-induced arthritis (pGIA mice), and human patients with RA. As a result, they discovered that a particular arginine residue of the citrullinated inter-α-trypsin inhibitor heavy chain (ITIH) 4 had been citrullinated in serum samples obtained from pGIA mice and some RA patients and, surprisingly, that the presence and the amount thereof would be correlated with onset and symptoms of arthritis. In addition, they verified that the levels of the C-reactive proteins, DAS28-CRP, and the rheumatoid factor were significantly high in RA patients comprising citrullinated ITIH4 in the serum. This has led to the completion of the present invention.

Specifically, the present invention provides the following.
1. A method for diagnosis of rheumatoid arthritis or a method for assisting diagnosis of rheumatoid arthritis in a subject, comprising detecting citrullination of an arginine residue of the inter-α-trypsin inhibitor heavy chain (ITIH) 4 in a biological sample obtained from the subject.
2. A method for monitoring disease activity of rheumatoid arthritis in a subject and/or therapeutic effects of an agent for rheumatoid arthritis comprising detecting citrullination of an arginine residue of the inter-α-trypsin inhibitor heavy chain (ITIH) 4 in a biological sample obtained from the subject.
3. The method according to 1 or 2, wherein the arginine residue is an arginine residue at position 438 in the amino acid sequence as shown in SEQ ID NO: 1 or 5.
4. The method according to any of 1 to 3, wherein the biological sample is a whole blood, plasma, serum, skin, or joint tissue sampled from the subject.
5. The method according to any of 1 to 4, wherein citrullination is detected by mass spectrometry, Western blot analysis, immunohistological detection, immunoprecipitation, or ELISA comprising recognizing a protein that contains citrulline.
6. The method according to any of 1 to 5, wherein citrullination is detected based on a bond with an antibody that binds to a modified protein having an amino acid sequence derived from the amino acid sequence as shown in SEQ ID NO: 1 or 5 by modification of arginine 438 into citrulline or a peptide fragment containing the citrulline.
7. A citrullinated protein derived from the protein having the amino acid sequence as shown in SEQ ID NO: 1 or 5 by modification of arginine 438 into citrulline or a fragment thereof comprising the citrulline.
8. A biomarker used for diagnosis of rheumatoid arthritis comprising the citrullinated protein or a fragment thereof according to 7.
9. An antibody that binds to the citrullinated protein or a fragment thereof according to 7 but does not bind to a noncitrullinated protein.
10. An agent for diagnosis of rheumatoid arthritis comprising the antibody according to 9.
11. A kit used for diagnosis or assistance for diagnosis of rheumatoid arthritis comprising the antibody according to 9.
12. A kit used for diagnosis or assistance for diagnosis of rheumatoid arthritis comprising the fragment comprising citrulline according to 7 as an internal standard used in mass spectrometry.

This description includes part or all of the content as disclosed in the description and/or drawings of Japanese Patent Application Nos. 2017-132888 and 2018-005038, which are priority documents of the present application.

Effects of the Invention

The present invention provides a novel biomarker for RA and a novel treatment target aimed at alleviating clinical symptoms of an RA patient.

BRIEF DESCRIPTION OF THE DRAWINGS

FIG. 2A shows the clinical scores for pGIA mice (mean±SEM, n=11); and FIG. 2B shows serious swelling observed at the joints of the front limb (the upper photograph) and the back limb (the lower photograph) of pGIA mouse in comparison with the control mouse (left photographs).

FIG. 3A shows the anti-pGPI antibody titer (n=6 to 9) and FIG. 3B shows the anti-CCP antibody titer (n=12 to 18) in serum samples obtained from mice into which CFA or pGPI had been injected. Each symbol indicates each mouse and a bar indicates mean±SEM. *: $p<0.05$, **: $p<0.01$.

FIG. 5A shows the results of Western blot analysis performed with the use of the AMC antibody; lanes 1 and 2: day 0; lanes 3 and 4: day 7; lanes 5 and 6: day 14; and lanes 7 and 8: day 28. FIG. 5B shows a chart indicating the 120 kD band intensity in Western blot analysis (n=3 to 6, mean±SEM).

FIG. 6A shows the results of Western blot analysis of the serum samples obtained from the pGIA mice (pGPI) or the control mice (CFA) on day 14. While the citrullinated protein was detected in the serum from the pGIA mice, it was not detected in the serum from the control mice; lanes 1 to 5: control mice; and lanes 6 to 10: pGIA mice. FIG. 6B shows the 120 kD band intensity in Western blot analysis. **: $p<0.01$.

FIG. 9 shows the results of analysis of separating the serum samples obtained from the pGIA mice (pGPI) and the control mice (CFA) 14 days after injection via SDS-PAGE, staining the resultants with Coomassie brilliant blue (A), and performing Western blot analysis with the use of the AMC antibody (B). G1 and G2: pGIA mouse samples; and C1 and C2: control mouse samples.

FIG. 10A shows the representative results of Western blot analysis of serum samples obtained from patients with rheumatoid arthritis (RA) and healthy subjects (HS); lanes 1 to 5: healthy subject samples; lanes 6 to 11: RA patient samples; and lane 12: pGIA mouse sample. FIG. 10B shows the 120 kD band intensity in Western blot analysis. Each symbol indicates each mouse. A bar indicates mean±SEM. **: $p<0.01$.

FIG. 13 shows some results of Western blot analysis performed with the use of the AMC antibody on serum samples obtained from: A: healthy subjects (HS: lanes 1-12); B: patients with osteoarthritis (OA: lanes 1-12); C: patients with systemic lupus erythematodes (SLE: lanes 1-15); and D: patients with Sjogren's syndrome (SS: lanes 1-11). In the case of the control patients with rheumatoid arthritis simultaneously subjected to analysis (RA, A: lane 13; B: lane 13; C: lane 16; and D: lane 12), a citrullinated protein was detected at a position of approximately 120 kD, but substantially no citrullinated protein was detected in healthy subjects and patients with other diseases. FIG. 13E shows some results of Western blot analysis performed with the use of the anti-ITIH4 antibody (left) and the AMC antibody (right) on serum samples obtained from healthy subjects (HS), patients with Sjogren's syndrome (SS), and patients with rheumatoid arthritis (RA). While a clear band was detected at a position of approximately 120 kD in the serum samples obtained from RA patients with the use of any antibody, no band was detected at a position of approximately 120 kD in the serum samples from HS and SS patients with the use of the AMC antibody.

FIG. 17A shows some results of Western blot analysis using the AMC antibody of serum samples obtained from patients with rheumatoid arthritis (RA) before treatment (−) and 24 hours after treatment (+) with biologics; lanes 1,2: abatacept; and lanes 3-8: infliximab. FIG. 17B shows the correlation between lowering of the citrullinated ITIH4 level and lowering of the DAS28-CRP level. r: correlation coefficient. FIG. 17C shows the correlation between lowering of the citrullinated ITIH4 level and lowering of the DAS28-ESR level. r: correlation coefficient.

EMBODIMENTS OF THE INVENTION

Figure 1:
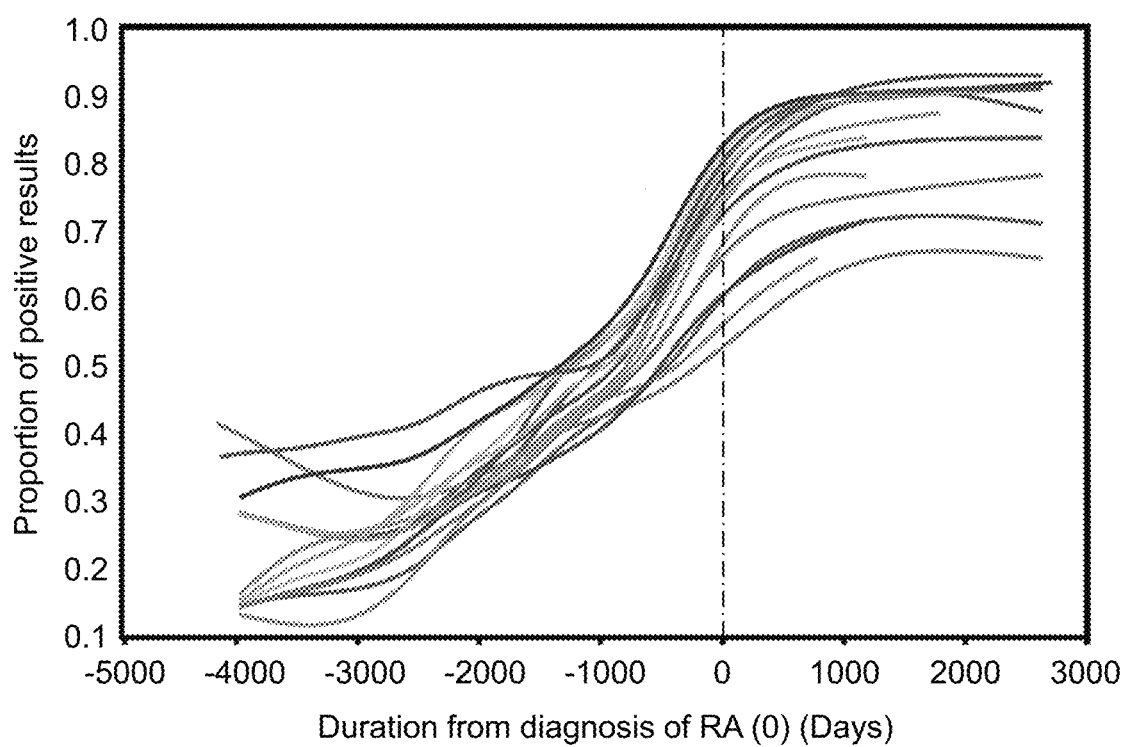
FIG. 1 shows the proportion of ACPA-positive subjects among 81 subjects who had been diagnosed to have rheumatoid arthritis (RA) with the use of serum samples obtained from the subjects before and after RA onset. The vertical axis indicates the proportion of antibody-positive subjects when 16 types of peptides are used as antigens: Apolipo E (277-296) cit2 cyclic; Biglycan (247-266) cit cyclic; Clusterin (221-240) cit cyclic; Clusterin (231-250) cit cyclic; Enolase (5-21) cit; Fibrinogen A (211-230) cit cyclic; Fibrinogen A (41-60) cit3 cyclic; Fibrinogen A (556-575) cit cyclic; Fibrinogen A (616-635) cit3 cyclic; Fibrinogen A-CIT; Filaggrin (48-65) cit2 cyclic; Histone 2A (1-20) cyclic; Histone 2B (62-81) cit cyclic; Histone 2B-CIT; Vimentin (58-77) cit3 cyclic; and Vimentin-CIT. The horizontal axis indicates a duration from the time point when RA is diagnosed (0) to the time point when the serum sample is obtained (a positive value indicates the number of days after diagnosis and a negative value indicates the number of days before diagnosis) (Sokolove et al., PLoS ONE, Vol. 7, Issue 5, e35296, 2012). Concerning the peptides mentioned above, "cit," "cit2," and "cit3" indicates that the number of citrulline residues is 1, 2, and 3, respectively, "CIT" indicates that citrullination occurs at the time of peptide synthesis, and "cyclic" indicates a cyclic peptide.

The present invention provides a method for diagnosis of rheumatoid arthritis or a method for assisting diagnosis of rheumatoid arthritis in a subject, comprising detecting citrullination of an arginine residue of the inter-α-trypsin inhibitor heavy chain (ITIH) 4 in a biological sample obtained from the subject. "Detection" of citrullination encompasses detection of the presence or an increase or decrease (i.e., variation) of citrullinated residues. The term "diagnosis of rheumatoid arthritis" used herein encompasses evaluation of rheumatoid arthritis onset, symptom progression, lowering of disease activity, alleviation of symptoms, effects of a therapeutic agent for rheumatoid arthritis, and other factors. The term "assistance (assisting)" for diagnosis can refer to provision of data necessary for diagnosis. The method according to the present invention can also be used as auxiliary diagnosis of rheumatoid arthritis showing a negative serum reaction to a rheumatoid factor and/or an anti-CCP antibody that have heretofore been used. Accordingly, the method according to the present invention may be performed in combination with diagnosis of rheumatoid arthritis involving the use of an anti-citrullinated antibody in a biological sample obtained from the subject as the index. The method according to the present invention comprises detecting, as a novel biomarker, a citrullinated ITIH4 protein in a sample obtained from the subject, such as a serum sample.

The method according to the present invention can comprise detecting citrullination of an arginine residue of the inter-α-trypsin inhibitor heavy chain (ITIH) 4 in a biological sample obtained from the subject and comparing the detected citrullination with citrullination of an arginine residue of the inter-α-trypsin inhibitor heavy chain (ITIH) 4 in a biological sample obtained from a healthy subject without rheumatoid arthritis. Alternatively, the method according to the present invention can comprise comparing the results of detection with the reference value prepared in advance. When a citrullinated arginine residue is present in the inter-α-trypsin inhibitor heavy chain (ITIH) 4 in a biological sample obtained from the subject or when the amount of citrullinated arginine residues is increased compared with the results of detection obtained from a healthy subject or the reference value, the subject can be determined to have rheumatoid arthritis.

An embodiment according to the present invention provides a method for monitoring disease activity of rheumatoid arthritis in a subject and/or therapeutic effects attained with the use of an agent for rheumatoid arthritis, comprising detecting citrullination of an arginine residue of the inter-α-trypsin inhibitor heavy chain (ITIH) 4 in a biological sample obtained from the subject.

The method for monitoring disease activity of rheumatoid arthritis and/or therapeutic effects attained with the use of an agent for rheumatoid arthritis comprises detecting citrullination a plurality of times, such as 2, 3, or more times and comparing the results of detection. In particular, the method for monitoring therapeutic effects comprises detecting citrullination at a plurality of time points including before treatment and after treatment with a therapeutic agent for rheumatoid arthritis and comparing the results of detection.

When citrullination is detected at a plurality of time points, an increased number of citrullinated residues, specifically, an increased amount of the citrullinated inter-α-trypsin inhibitor heavy chain (ITIH) 4, indicates a more advanced disease state. In contrast, a decreased number of citrullinated residues, specifically, a decreased amount of the citrullinated inter-α-trypsin inhibitor heavy chain (ITIH) 4, indicates alleviation. When citrullination is detected before and after treatment with the agent for rheumatoid arthritis and a decreased number of citrullinated residues, specifically, a decreased amount of the citrullinated inter-α-trypsin inhibitor heavy chain (ITIH) 4, is detected, such decrease indicates that therapeutic effects are achieved by the agent for rheumatoid arthritis.

Subjects of the method according to the present invention can be, for example, mammalian animals, such as humans, monkeys, dogs, cats, bovines, horses, mice, rats, and rabbits. In the case of human subjects, in particular, the method according to the present invention is performed for diagnosis of rheumatoid arthritis in humans. Alternatively, subjects are non-human mammalian animals such as mice, and the method according to the present invention can target animal models of intentionally induced rheumatoid arthritis.

In the present invention, target biological samples of the detection are selected from whole blood, plasma, serum, skin, and joint tissue sampled from the subjects.

The inter-α-trypsin inhibitor is a trypsin inhibitor protein family molecule existing in the mammalian plasma, and it is a glycoprotein also existing in fowl and fish. The inter-α-trypsin inhibitor is known to have a composite structure comprising a common light chain referred to as "bikunin" bound to several heavy chains (ITIH1 to ITIH6) and have inhibitory activity on proteases such as trypsin and chymotrypsin. ITIH4 that was found by the present inventors to be correlated with disease activity of rheumatoid arthritis is a type of the heavy chain domain, although the function thereof in vivo was not elucidated completely.

Citrulline is a type of an amino acid constituting the uric acid cycle and it has the IUPAC name: 2-amino-5-(carbamoylamino)pentanoic acid. A protein naturally occurring in the body of mammalians and the like is composed of 20 types of L-amino acids, and citrulline is not included therein. Accordingly, it is known that citrulline is not present in the protein immediately after translation and that an arginine residue in the translated protein is converted into a citrulline residue by peptidylarginine deiminase (PAD). This post-translational modification from arginine to citrulline is generally referred to as "citrullination."

Activity of PAD in vivo is considered necessary for cell regeneration or other purposes, and the correlation of protein citrullination with aging is also reported. Thus, various types of citrullinated proteins exist in vivo and a protein may comprise a plurality of arginine residues that can be citrullinated. By detection of ACPA that is currently employed in diagnosis of rheumatoid arthritis, a plurality of antibodies having specificity to such citrullinated proteins are collectively detected. Thus, the results of detection may indicate a low correlation with disease activity.

The present inventors discovered that citrullination in ITIH4, which had not been reported in the past, is highly correlated with disease activity of rheumatoid arthritis.

Mouse ITIH4 is a protein having the amino acid sequence consisting of 942 amino acids as shown in SEQ ID NO: 1 (UniProtKB accession No.: A6X935). While SEQ ID NO: 1 comprises a plurality of arginine residues, it was found preferable to select arginine 438 in SEQ ID NO: 1 to detect the occurrence of citrullination by the method according to the present invention.

Human ITIH4 is a protein having the amino acid sequence consisting of 930 amino acids as shown in SEQ ID NO: 5 (UniProtKB accession No.: Q14624). While SEQ ID NO: 5 comprises a plurality of arginine residues, it was found preferable to select arginine 438 in SEQ ID NO: 5 as with the case of mouse ITIH4 to detect the occurrence of citrullination by the method according to the present invention.

The amino acid sequences as shown in SEQ ID NO: 1 and SEQ ID NO: 5 are encoded by the ITIH4 gene, and such amino acid sequences comprise signal peptides. A person skilled in the art understands that a protein generally has isoforms. Accordingly, it should be understood that the human ITIH4 protein intended by the present inventors encompasses mature proteins that can function in vivo and a plurality of protein isoforms, in addition to the protein consisting of the amino acid sequence as shown in SEQ ID NO: 5.

The amino acid sequence of human ITIH4 is highly homologous to the amino acid sequence of mouse ITIH4 (65% homology), and the sequence of a region including arginine 438 of the former is very similar to that of the latter. Such phenomena are observed in a wide variety of mammalian animals. On the basis of the sequence information obtained from the database managed by the National Center for Biotechnology Information, NCBI, U.S.A., for example, the amino acid sequence information on ITIH4 of mammalian animals other than humans and mice is obtained, and the obtained sequence information is subjected to alignment analysis with the amino acid sequences as shown in SEQ ID NO: 1 and SEQ ID NO: 5. Thus, an arginine residue corresponding to arginine 438 in SEQ ID NO: 1 and SEQ ID NO: 5 can be identified.

A method of detecting citrullination in ITIH4 is not particularly limited, provided that a citrullinated protein or peptide can be distinguished from a non-citrullinated protein or peptide. For example, detection can be performed via mass spectrometry or an immunological method, such as Western blot analysis, immunohistochemical detection, immunoprecipitation, or ELISA.

Hereafter, a citrullinated protein comprising an amino acid sequence derived from the amino acid sequence as shown in SEQ ID NO: 1 or 5 by modification of arginine 438 into citrulline is occasionally referred to as the "citrullinated ITIH4 protein" for convenience of description.

<Mass Spectrometry>

When protein analysis is performed via mass spectrometry, in general, a sample before being subjected to mass spectrometry (MS) is separated and concentrated via liquid chromatography (LC), and LC-MS/MS performing LC in combination with tandem mass spectrometry can also be used for the analysis.

When detecting citrullination of ITIH4 via mass spectrometry, for example, analysis can be performed using, as a signature peptide, a peptide consisting of the amino acid sequence as shown in SEQ ID NO: 3 or 7.

The peptide represented by SEQ ID NO: 3 (MALDNG-GLAR) consists of 10 amino acids corresponding to amino acids 429 to 438 in SEQ ID NO: 1. This peptide can be obtained by digesting the mouse ITIH4 protein with trypsin. That is, this peptide is a peptidase (trypsin)-digested fragment comprising arginine 438 in SEQ ID NO: 1. A peptide derived from the peptide represented by SEQ ID NO: 3 by citrullination of arginine 10 can serve as a signature peptide for detecting the mouse citrullinated ITIH4 protein. SEQ ID NO: 4 shows the amino acid sequence of the peptide mentioned above.

The peptide represented by SEQ ID NO: 7 (LALDNG-GLAR) consists of 10 amino acids corresponding to amino acids 429 to 438 in SEQ ID NO: 5. This peptide can be obtained by digesting the human ITIH4 protein with trypsin. That is, this peptide is a peptidase (trypsin)-digested fragment comprising arginine 438 in SEQ ID NO: 5. A peptide derived from the peptide represented by SEQ ID NO: 7 by citrullination of arginine 10 can serve as a signature peptide for detecting the human citrullinated ITIH4 protein. SEQ ID NO: 8 shows the amino acid sequence of the peptide mentioned above.

As a person skilled in the art understands, trypsin cleaves a protein at positions that are the C-terminal side of lysine and arginine and not adjacent to proline in the amino acid sequence of the protein. Among numerous fragments obtained by digesting ITIH4 with trypsin, accordingly, peptides represented by SEQ ID NO: 3 and SEQ ID NO: 7 can be fragments containing arginine 438. Accordingly, trypsin-digested fragments that are preferably used in mass spectrometry are peptides represented by SEQ ID NO: 3 and SEQ ID NO: 7. Also, peptides represented by SEQ ID NO: 4 and SEQ ID NO: 8 can be used for detecting citrullination of arginine 438.

For detection via mass spectrometry, at the outset, it is necessary to remove substances other than analytes from biological samples obtained from the subjects to a maximum extent and dissolve the analytes in an adequate solvent. To this end, an ITIH4-containing fraction or gel is obtained via, for example, centrifugation or gel electrophoresis. Subsequently, the resultant is degraded into a peptide with the aid of a protease such as trypsin. The sample before being subjected to mass spectrometry can further be separated via LC in order to improve accuracy of analysis.

Mass spectrometry is capable of amino acid sequence determination. Accordingly, whether or not a peptide fragment is the peptide fragment of interest can be determined. In addition, the peptide fragment concentration in the sample can be determined based on the peak intensity.

Methods of ionization in mass spectrometry are not particularly limited. For example, electron ionization (EI), chemical ionization (CI), field desorption (FD), fast atom bombardment (FAB), matrix assisted laser desorption/ionization (MALDI), or electrospray ionization (ESI) can be adopted. Methods of analysis of ionized samples are not particularly limited, and magnetic sector-type, quadrupole (Q)-type, ion trap (IT)-type, time of flight (TOF)-type, Fourier transform ion cyclotron resonance (FT-ICR), or other methods can be adequately employed in accordance with the method of ionization. Further, a triple quadrupole mass spectrometer or the like may be used to perform MS/MS analysis or multiple-stage mass spectrometry of 3 (MS3) or more stages.

An apparatus that can be used for the method according to the present invention is not particularly limited. For example, the nanoAcquity Ultra-performance LC (UPLC) system (Waters Co.) can be used in combination with the Q-TOF mass spectrometer (Synapt high definition mass spectrometry system, Waters).

Citrullination of arginine residues can be identified via mass spectrometry with reference to the databases including mass spectrometry data of modified peptides such as citrullinated peptides in addition to the mass spectrometry data of general peptides.

According to need, a sample can be concentrated or diluted before subjected to analysis. For the purpose of quantification, it is preferable to prepare a calibration curve in advance with the use of, as the internal standard, the peptide represented by SEQ ID NO: 3 or SEQ ID NO: 7 and the peptide represented by SEQ ID NO: 4 or SEQ ID NO: 8 derived from the peptide represented by SEQ ID NO: 3 or SEQ ID NO: 7 by citrullination of arginine at the C terminus.

<Immunological Method>

Immunological methods that can be adopted for analysis of the citrullinated protein are not limited, and examples thereof include Western blot analysis, immunohistological detection, immunoprecipitation, and ELISA. Such methods can be performed with the use of an antibody reacting with the citrullinated ITIH4 protein. Accordingly, such method can comprise detecting citrullination based on the binding with an antibody that binds to a modified protein comprising an amino acid sequence derived from the amino acid sequence as shown in SEQ ID NO: 1 or 5 by modification of arginine 438 into citrulline or a peptide fragment including such citrulline residue.

Detection by Western blotting comprises developing a biological sample that may contain the ITIH4 protein via SDS-PAGE, transferring the protein to a hydrophobic membrane, and detecting citrullination in a band with the use of an anti-citrullinated protein antibody.

Immunohistological detection comprises immobilizing a tissue section sampled from a subject and visualizing the binding between the citrullinated ITIH4 protein and an antibody reacting thereto. Examples of method of visualization include autoradiography, the gold colloid method, the fluorescent antibody method, and the enzyme antibody method. An antibody binding to the citrullinated ITIH4 protein may be directly labeled, or a labeled secondary antibody may be used.

Immunoprecipitation comprises subjecting the citrullinated ITIH4 protein in the biological sample such as a serum sample to a reaction with an antibody against the protein to form a complex, allowing the complex to bind to Protein A or G or a secondary antibody immobilized on a bead, and separating the substance bound thereto from the substance unbound thereto.

ELISA comprises performing an antigen-antibody reaction, measuring enzyme activity using the enzyme-labeled primary or secondary antibody, and converting the measured enzyme activity into the numerical value. Examples of known ELISA techniques include the direct method, the indirect method, the sandwich method, and the competition method, and such techniques are extensively employed for detection and quantification in the art.

An anti-citrullinated protein antibody that can be used in the immunological method may be an antibody that can bind to a plurality of citrullinated proteins when, for example, a sample or a separated fraction may contain no or substantially no citrullinated proteins other than the ITIH4 protein. In such a case, for example, a polyclonal anti-citrullinated protein antibody commercialized by Abcam Plc can be used. As described in the examples below, alternatively, it is also possible to use an anti-modified citrulline monoclonal (AMC) antibody that recognizes, as an antigen, a colored substance generated by heating citrulline with a color reagent in a strong acid.

When a sample may comprise a plurality of citrullinated proteins and such proteins are to be detected without separating them from one another, in contrast, it is preferable to use an antibody that can bind specifically to the citrullinated ITIH4 protein. A method for obtaining such antibody is described below.

When the citrullinated ITIH4 protein and a fragment thereof comprising a citrulline residue are detected in a biological sample obtained from the subject, the subject can be determined to have rheumatoid arthritis or exhibit a high disease activity level of rheumatoid arthritis. When detection is carried out at a plurality of time points and an increased amount of the citrullinated ITIH4 protein and a fragment thereof comprising a citrulline residue is observed in the biological sample, rheumatoid arthritis can be determined to have advanced in the subject. When a decrease is detected, in contrast, rheumatoid arthritis can be determined to have been alleviated.

The method according to the present invention can further comprise comparing the results of detection of the citrullinated ITIH4 protein and a fragment thereof comprising a citrulline residue in the biological sample with the reference value prepared for determination of rheumatoid arthritis in advance. The "reference value" employed for determination of onset and/or severity of rheumatoid arthritis can be obtained in the form of, for example, the concentration of the citrullinated ITIH4 protein in the serum, the amount of the antibody binding to the citrullinated ITIH4 protein (e.g., the absolute amount or the fluorescence intensity derived from the label), or the peak area determined via LC/MS. Alternatively, the "reference value" can be calculated based on the band intensity detected via Western blotting.

For example, the citrullinated ITIH4 protein or a fragment thereof comprising a citrulline residue is detected in patients with rheumatoid arthritis and healthy subjects, or 2 groups of patients classified on the basis of the severity (i.e., the severe case group and the mild case group) from the viewpoint of the correlation with clinical symptoms, and the cut-off values that are obtained by a statistic method from the detection results can be used as the reference value.

With the use of the reference value, the conditions of a patient with rheumatoid arthritis, such as severity, can be evaluated on the basis of the results of detection from the sample obtained from the patient. When the result of detection of the citrullinated ITIH4 protein and a fragment thereof comprising a citrulline residue from a subject is higher than the reference value, whether or not the subject has rheumatoid arthritis and the severity of rheumatoid arthritis can be evaluated.

The method according to the present invention comprises detecting the citrullinated ITIH4 protein in a biological sample in vitro. In addition to the initial diagnosis, accordingly, the method according to the present invention can be adequately employed for evaluation of, for example, disease progression and therapeutic effects attained with the use of the agent for rheumatoid arthritis, according to need.

Rheumatoid arthritis is an autoimmune disease. As agents for treatment of rheumatoid arthritis that are currently used, accordingly, immunosuppressive agents such as methotrexate, immunomodulators, steroids, and biologics are known. Examples of known biologics include monoclonal antibodies that target tumor necrosis factors (TNF)-α, such as infliximab and adalimumab, and abatacept that inhibits T cell activation.

Another aspect of the present invention provides a method for treatment of rheumatoid arthritis in a subject comprising administering the agent for treatment of rheumatoid arthritis to a subject who was evaluated to have rheumatoid arthritis by the method according to the present invention described above.

The present inventors found that the citrullinated ITIH4 protein level would decrease in the serum derived from a patient whose symptoms have been alleviated by the treatment with the use of the agent for treatment of rheumatoid arthritis. The present inventors also verified that a fluctuation in the citrullinated ITIH4 protein level in the serum was highly correlated with the existing composite disease activity index, such as DAS28. This further verifies that the method according to the present invention can serve as a more effective disease activity index. A conventional disease activity index, such as DAS28, is obtained by complicated calculation using a plurality of parameters. The method according to the present invention, however, is intended to measure a single parameter; i.e., the citrullinated ITIH4 protein in the serum, and it thus enables diagnosis and monitoring in a simple manner.

ACPA, which is used for RA diagnosis at present, increases before the RA onset (FIG. 1) and when evaluated positive as a result of the test, it is not examined again thereafter. According to the method of the present invention, in contrast, the abundance of the citrullinated ITIH4 protein is increased or decreased in correlation with the disease activity. Accordingly, the method according to the present invention can be employed for evaluation of or monitoring the disease activity after RA onset; i.e., the disease state, in addition to the test before RA onset and at an early stage after RA onset, with the use of the citrullinated ITIH4 protein or a fragment thereof as a biomarker for RA diagnosis. In addition, the method according to the present invention can be employed as a method for evaluation of the severity of RA and can obtain and provide the data for RA diagnosis.

<Citrullinated ITIH4 Protein>

The present invention also provides a citrullinated ITIH4 protein derived from the protein having the amino acid sequence as shown in SEQ ID NO: 1 or 5 by modification of arginine 438 into citrulline or a fragment thereof comprising the citrulline residue. The citrullinated ITIH4 protein or a fragment thereof is an isolated protein or a fragment thereof.

The citrullinated ITIH4 protein or a fragment thereof according to the present invention can be used for RA diagnosis or assistance for RA diagnosis by detecting the presence thereof in a biological sample obtained from the subject. Also, the citrullinated ITIH4 protein or a fragment thereof according to the present invention can be used as a biomarker serving as the disease activity index for RA.

Accordingly, the present invention can provide a biomarker used for diagnosis of rheumatoid arthritis comprising the citrullinated ITIH4 protein or a fragment thereof according to the present invention. By detecting the biomarker in a biological sample obtained from the subject, the data as to whether or not the subject has rheumatoid arthritis can be obtained.

As described above, the sequences represented by SEQ ID NO: 1 and SEQ ID NO: 5 each comprise a plurality of arginine residues. As long as arginine 438 is citrullinated, other arginine residues may or may not be citrullinated in the citrullinated ITIH4 protein according to the present invention. Also, other amino acid residues may have other post-translational modification. Accordingly, examples of the citrullinated ITIH4 protein according to the present invention include, but are not particularly limited to, proteins having amino acid sequences as shown in SEQ ID NO: 2 and SEQ ID NO: 6 derived from the amino acid sequences as shown in SEQ ID NO: 1 and SEQ ID NO: 5 only by modification of arginine 438 into citrulline.

The fragment according to the present invention may be any fragment of the citrullinated ITIH4 protein comprising a citrullinated amino acid at position 438. For example, such fragment can comprise 3, 4, 5, 6, 7, 8, 9, 10, 15, 20, 25, 30, or more amino acids including amino acid 438, which is a citrullinated arginine, in the sequence as shown in SEQ ID NO: 1 or SEQ ID NO: 5. Specifically, such fragment can comprise amino acids 421 to 450, 428 to 447, or 429 to 438 having citrulline at position 438 in the sequence as shown in SEQ ID NO: 5. Such fragment can be a fragment consisting of, for example, the amino acid sequence as shown in SEQ ID NO: 4 or SEQ ID NO: 8.

When the citrullinated ITIH4 protein is detected via mass spectrometry and used for diagnosis or assistance for diagnosis of rheumatoid arthritis, for example, it is preferable to perform detection with the use of, as a signature peptide, a peptide fragment having an amino acid sequence (SEQ ID NO: 4 or 8) derived from the amino acid sequence as shown in SEQ ID NO: 3 or 7 via citrullination at the C terminus.

<Antibody>

The present invention provides an antibody that binds to the citrullinated ITIH4 protein or a fragment thereof according to the present invention but does not bind to a noncitrullinated protein. The antibody according to the present invention has binding specificity to the citrullinated ITIH4 protein or a fragment thereof, so as to perform diagnosis of rheumatoid arthritis by detecting the citrullinated ITIH4 protein or a fragment thereof in vitro.

Preferably, the antibody according to the present invention binds to a protein derived from the protein having the amino acid sequence as shown in SEQ ID NO: 1 or 5 by modification of arginine 438 into citrulline (i.e., the citrullinated ITIH4 protein, such as a protein having the amino acid sequence as shown in SEQ ID NO: 2 or 6) or a fragment comprising citrulline at position 438 (e.g., a peptide having the amino acid sequence as shown in SEQ ID NO: 4 or 8), but it does not bind to a protein that does not comprise citrulline at position 438 (e.g., a protein having the amino acid sequence as shown in SEQ ID NO: 1 or 5) or a fragment thereof (e.g., a peptide having the amino acid sequence as shown in SEQ ID NO: 3 or 7).

The terms "binds" and "specifically binds" herein may mean that the binding affinity between an antigen and an antibody is a KD value of $10^{-8}$ M or lower, preferably $10^{-9}$ M or lower, and more preferably $10^{-10}$ M or lower, although the binding affinity is not limited thereto. Accordingly, the antibody according to the present invention shows the binding affinity as described above to a protein derived from the protein having the amino acid sequence as shown in SEQ ID NO: 1 or 5 by modification of arginine 438 into citrulline (the citrullinated ITIH4 protein) or a fragment thereof comprising citrulline at position 438, but it does not show the binding affinity as described above to a protein that does not comprise citrulline at position 438 or a fragment thereof.

With the use of a common expression in the art, specifically, the antibody according to the present invention recognizes an epitope comprising citrulline at position 438, which is citrullinated from arginine at position 438 in the sequence as shown in SEQ ID NO: 1 or 5.

The antibody according to the present invention can be preferably used for RA diagnosis or assistance for RA diagnosis. The antibody according to the present invention can also be used as a therapeutic agent for alleviating clinical symptoms of RA.

The antibody according to the present invention may be a polyclonal or monoclonal antibody, provided that it binds specifically to the citrullinated ITIH4 protein or a fragment thereof according to the present invention, with a monoclonal antibody being preferable. Also, the antibody according to the present invention is intended to be used for RA diagnosis or assistance for RA diagnosis. Accordingly, the antibody according to the present invention may be a non-human antibody, such as a mouse, rabbit, or goat antibody, a chimeric antibody, a humanized antibody, or a human antibody without particular limitation.

When an antigen is identified, a method for producing an antibody is well-known in the art. The antibody according to the present invention can be obtained in the form of a polyclonal antibody in accordance with a conventional technique, by immunizing a non-human mammalian animal with the citrullinated ITIH4 protein or a fragment thereof identified as the antigen. A monoclonal antibody can be obtained from a hybridoma resulting from fusion between an antibody-producing cell that produces an antibody reacting with the citrullinated ITIH4 protein with a myeloma cell. It is important to avoid selecting a hybridoma clone that can bind to the protein having the amino acid sequence as shown in SEQ ID NO: 1 or 5; i.e., the protein in which arginine 438 is not citrullinated, or a fragment thereof.

The antibody according to the present invention can also be obtained via genetic engineering or chemical synthesis on the basis of the amino acid sequence information of the antibody according to the present invention with verified activity or the nucleotide sequence information of a polynucleotide encoding such antibody. When another antibody is produced on the basis of the sequence information of the antibody with verified activity, an antibody having the binding affinity that is the same or equivalent to that of the original antibody can be produced on the basis of the sequence of the complementary determination region (CDR) of the original antibody. An antibody having higher binding affinity can also be produced.

When producing an antibody via genetic engineering, a polynucleotide encoding the heavy chain and a polynucleotide encoding the light chain can be introduced into an adequate host cell and expressed therein to obtain an antibody of interest in the form of a recombinant protein. In such a case, a polynucleotide may be DNA or RNA, and it may be introduced into a host cell in accordance with a conventional technique in the art. According to need, a polynucleotide can be introduced into a host cell with the use of a vector, for example, a virus vector, a plasmid vector, or a phage vector. Examples of host cells that can be used include bacteria such as E. coli, yeast cells, insect cells, and animal cells. A polynucleotide encoding the heavy chain and a polynucleotide encoding the light chain may be introduced into separate vectors, or they may be ligated to each other and introduced into the same vector.

For example, cDNAs encoding the heavy chain and the light chain of the antibody according to the present invention may be integrated into a vector comprising a signal sequence, a poly-A sequence, a regulatory sequence such as a promoter sequence, and a selection marker, according to need. The vector may be introduced to an adequate host cell, and the host cell may be cultured. Thus, an antibody capable of specifically recognizing the citrullinated protein or a fragment thereof can be obtained in the form of a recombinant protein.

The antibody according to the present invention is produced in the manner described above. For example, it may be a recombinant protein obtained via genetic engineering or a protein obtained via chemical synthesis.

When the antibody according to the present invention is used in the form of a monoclonal antibody, the antibody can be an IgG antibody molecule, an IgM antibody molecule, an antigen-binding fragment of such antibody molecule, or an antigen-binding derivative of such antibody molecule. For example, the antibody can be a complete antibody, an Fab fragment, an Fab' fragment, an F(ab')$_2$ fragment, a single-stranded antibody (scFv) fragment comprising a heavy chain variable (VH) region ligated to a light chain variable (VL) region with a linker, scFv-Fc, sc(Fv)$_2$, Fv, or a diabody.

scFv, scFv-Fc, and sc(Fv)$_2$ are each a synthetic polypeptide comprising variable regions ligated to each other via a linker. Any linker that is generally used in the art can be used without particular limitation. For example, a peptide linker comprising 5 to 25, and preferably 10 to 20 amino acid residues, such as a GS linker, can be preferably used.

The antibody according to the present invention encompasses a derivative known to a person skilled in the art, such as a derivative modified to facilitate antibody purification or enhance stability, provided that antigen-binding specificity is not affected. A fragment and a derivative thereof that retain binding specificity to the citrullinated protein or a fragment thereof are to be included within the scope of the "antibody" herein for convenience, unless there is anything repugnant in the context.

The antibody according to the present invention can also be synthesized in the form of a multimeric antibody, such as a dimer, trimer, or tetramer. In addition, the antibody according to the present invention may be a bispecific antibody having the first binding specificity to a citrullinated protein or a fragment thereof and the second binding specificity to other antigens. A person skilled in the art is able to obtain the antibody according to the present invention in the form adequate for relevant application on the basis of the description of the present application and the general technical knowledge in the art.

In addition, the antibody according to the present invention may be labeled for detection. Labelling may be, for example, fluorescence labeling, enzyme labeling, or radioactive labeling, although labelling is not particularly limited thereto.

<Diagnostic Agent for Rheumatoid Arthritis>

The present invention provides an agent for diagnosis of rheumatoid arthritis used for detecting the citrullinated ITIH4 protein in a biological sample obtained from the subject. The agent for diagnosis of rheumatoid arthritis is preferably capable of detecting a protein comprising an amino acid sequence derived from the amino acid sequence as shown in SEQ ID NO: 1 or 5 by modification of arginine 438 into citrulline or such citrulline residue. It is particularly preferable that the agent for diagnosis comprise an antibody capable of binding to an epitope comprising such citrullinated residue.

<Kit>

The present invention further provides a kit used for diagnosis or assistance for diagnosis of rheumatoid arthritis.

The kit can comprise, for example, the antibody according to the present invention. The kit may be used for detection via ELISA, for example. In addition to the antibody according to the present invention, the kit can adequately comprise a reagent for binding and detecting the bond between a citrullinated ITIH4 protein or a citrullinated ITIH4 peptide in a biological sample and the antibody according to the present invention capable of binding thereto, such as a reaction solution, a wash solution, an enzyme-labeled secondary antibody, a color substrate, a positive control, a negative control, a reaction vessel such as a microtiter plate, and the instructions. The kit can comprise the labeled antibody according to the present invention. The kit can also comprise the antibody according to the present invention in combination with the labeled secondary antibody capable of binding to the antibody according to the present invention.

The kit can be used for detection via mass spectrometry. For example, the kit can adequately comprise a peptidase such as trypsin, an eluate used for LC, a citrullinated peptide fragment to be detected as the internal standard (specifically, the peptide fragment represented by SEQ ID NO: 4 or 8), and instructions containing information such as conditions for mass spectrometry of such fragment.

Various kits used for detection of antigens involving the use of the antigen-antibody reaction are commercially available. A person skilled in the art would readily conceive of constitutional elements to be included in the kit and constitutional elements preferably included in the kit.

EXAMPLES

Hereafter, the present invention is described in greater detail with reference to the examples, although the scope of the present invention is not limited to these examples.

Reference Example 1: Induction of Arthritis in Mice

DBA/1 mice (6- to 10-week-old) were immunized with 25 µg of peptide GPI$_{325-339}$ (pGPI, Invitrogen) emulsified in the Complete Freund's adjuvant (CFA) (Becton Dickinson) at a volume ratio of 1:1 via endodermic injection in the area of the tail root. In order to develop arthritis, 200 ng of pertussis toxin (Sigma-Aldrich) was intraperitoneally injected into each mouse 0 day and 2 days after immunization. CFA containing no pGPI was selectively injected into the control mice.

The mice into which pGPI had been injected (the pGIA mice) and the control mice were evaluated as to arthritis every other day, and swelling and reddening of each limb were evaluated on a 0 to 3 scale. As described in Iwanami K. et al., Arthritis Res. Ther., 2008; 10: R130, evaluation was made on the basis of the total scores of the four limbs as the clinical scores.

As a result, symmetrical polyarthritis was induced in all the pGPI-immunized mice, and serious swelling was observed in the ankle joints of the front limbs and the back limbs, as shown in FIG. 2A. Arthritis was observed 8 days after immunization, the most serious symptom was observed 14 days after immunization, and then the symptom disappeared slowly. As shown in FIG. 2B, no swelling was observed in the control mice, but apparent swelling was observed in the pGIA mice 14 days after immunization. Thus, the symptom was confirmed to be pGPI-induced arthritis.

Example 1: Expression of Autoantibody in Serum of Peptide GPI-Induced Arthritis Mice Serum samples were obtained from the pGIA mice and the control mice, and the anti-pGPI antibody titer and the anti-citrullinated protein antibody (ACPA/anti-CCP antibody) titer were measured via ELISA.

In order to measure the anti-pGPI antibody, a 96-well plate (Nunc, MaxiSorp) was coated with 5 µg/ml of pGPI at 4° C. over the period of 12 hours, the plate was washed 3 times with a wash buffer (PBS with 0.05% Tween 20), the blocking solution (PBS containing 1% bovine serum albumin) was added thereto, and the resultant was allowed to stand at room temperature for 1 hour to block non-specific binding. After washing, 100 µl of the diluted serum (250-fold to 12,000-fold diluted) was added thereto, and the resultant was allowed to stand at room temperature for 2 hours.

In order to measure the anti-CCP antibody, a 25-fold diluted serum sample was applied to a 96-well plate pre-coated with a cyclic citrullinated peptide (CCP) included in a commercialized kit (Immunoscan CCPlus test kit, Euro Diagnostica), and the resultant was allowed to stand at room temperature for 1 hour.

After incubation, the plate was washed, horseradish peroxidase (HRP)-conjugated rabbit polyclonal anti-mouse immunoglobulin (Dako) was adequately diluted and added to the plate, and incubation was carried out at room temperature for 1 hour (pGPI) or 30 minutes (CCP). Subsequently, the plate was washed, the TMB microwell peroxidase substrate (KPL) was added to develop color, and the optical density at 450 nm was measured using a microplate reader.

As a result, the anti-pGPI antibody was first detected in the serum samples obtained from the pGIA mice 14 days after the immunization, and the antibody level was then elevated, although no elevation was observed in the samples obtained from the control mice. A significant difference was observed between the results of the pGIA mice and those of the control mice from 14 days after immunization (FIG. 3A).

The ACPA titer in the serum of the pGIA mice began to elevate gradually 14 days after immunization, and it was significantly higher than that of the control mice from 21 days after immunization (FIG. 3B).

On the basis of the elevated antibody titer against citrullinated protein, some citrullinated proteins were deduced to increase in the serum because of the arthritis of interest, although specific citrullinated proteins were not yet identified. Thus, citrullinated protein expression in a plurality of tissue samples obtained from pGIA mice was then evaluated.

Example 2: Increased Citrullinated Protein in pGIA Mice

CFA or pGPI was injected into mice, tissue samples were collected from the mice through the ankle joints of the back limbs, the tail skin through which CFA or pGPI had been injected, the lung, the spleen, and the lymph node 0, 7, 14, and 28 days after injection. The samples were fixed with 10% formalin and embedded in paraffin, and tissue sections were then prepared.

For immunohistological analysis, Reagent A (20% $H_2SO_4$, 25% $H_3PO_4$, and 0.025% $FeCl_3$) and Reagent B (1% diacetylmonooxime, 0.5% antipyrine, and 1 M acetic acid) were mixed to each other at the volume ratio of 2:1 to prepare a modification buffer. The modification buffer was added to each section, and the resultant was then incubated at 37° C. for 2.5 hours in a light-shielded container to modify a citrulline residue. Thereafter, incubation was further carried out using the rabbit anti-modified citrulline (AMC) antibody (provided by Dr. Ishigami, Tokyo Metropolitan Institute of Gerontology, diluted 3,200-fold with PBS containing 2% BSA) at room temperature overnight. Subsequently, HRP-conjugated goat anti-rabbit IgG (H+L) (Bio-Rad) was added as a secondary antibody, and incubation was then carried out at room temperature for 30 minutes.

Figure 4:
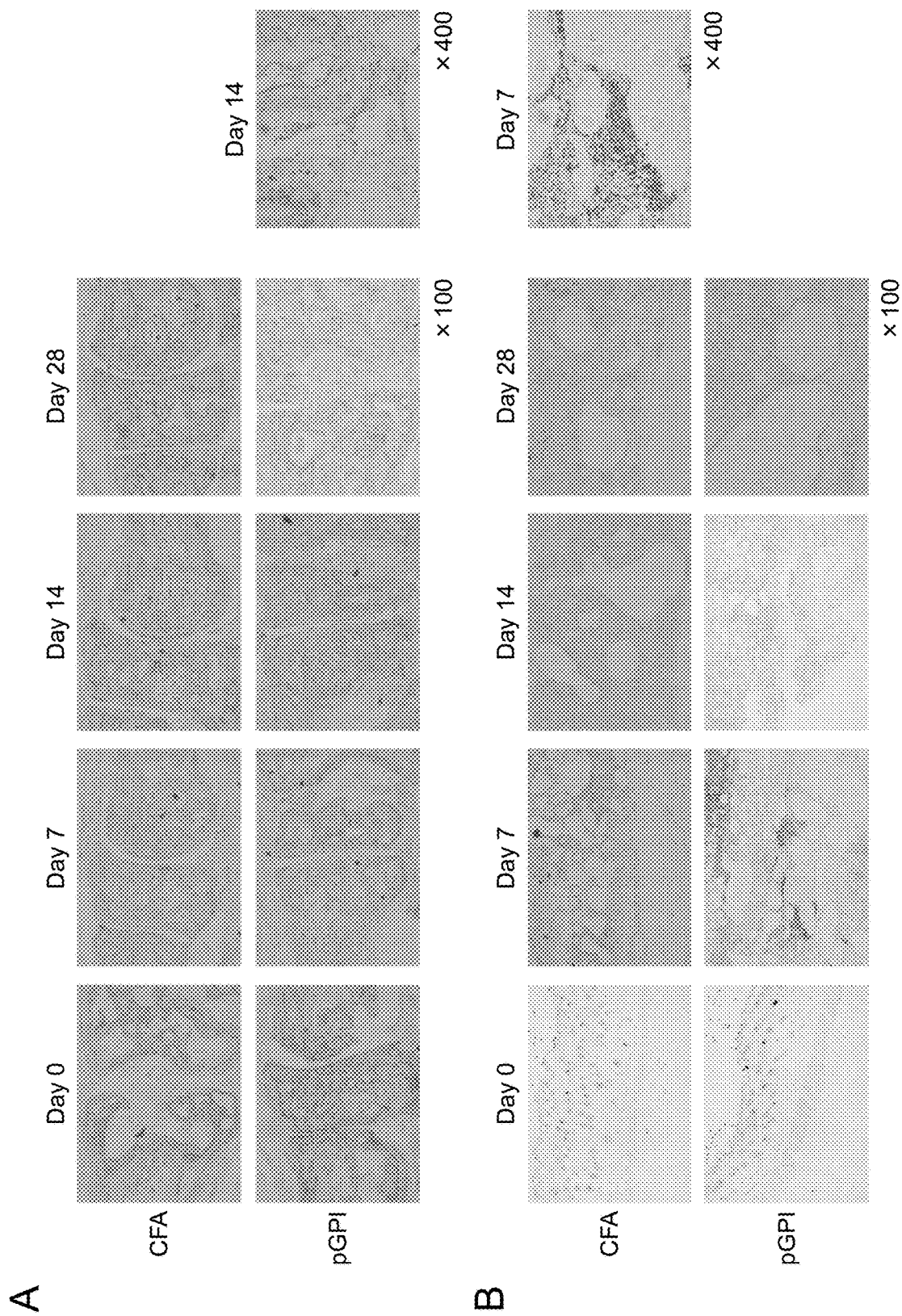
FIG. 4 shows the results of immunohistochemical staining of the joint and skin sections using the AMC antibody. While no change was observed in the mice into which CFA had been injected, citrullinated proteins were detected at the joint (A) and in the skin (B) of the mice into which pGPI had been injected 14 days and 7 days after injection, respectively. The enlarged views of the joint 14 days after injection and the skin 7 days after injection are shown in the right.

As a result of immunohistological detection of modified citrullinated residues, the citrullinated protein was detected at the joint of the mice into which pGPI had been injected 14 days after immunization (FIG. 4A), and protein expression was observed in the region of synovial hyperplasia. The citrullinated protein was detected in the skin 7 days after immunization (FIG. 4B), and this protein expression was observed in inflammatory cells invading the subcutaneous tissue surrounding the site of injection (data not shown). No citrullinated protein was detected in other tissues such as lung, spleen, or lymph node (data not shown). Also, no citrullinated protein was detected in any tissue of the mice into which CFA only had been injected.

The elevated citrullinated protein expression was detected in the skin (i.e., 7 days after immunization) earlier than that at the joint (i.e., 14 days after immunization). Thus, citrullinated protein production in the skin was considered to be one of the triggers for the induction of arthritis.

Example 3: Detection of Citrullinated Protein in Serum of pGIA Mice 1

The serum samples collected from the pGIA mice were analyzed via Western blotting using the AMC antibody used in Example 1.

The serum samples were obtained from the pGPI- or CFA-immunized mice 0, 7, 14, and 28 days after immunization, 50 µg/well of serum samples were loaded, sodium dodecyl sulfate-polyacrylamide gel electrophoresis (SDS-PAGE) was performed, and the resultant was transferred to a polyvinylidene fluoride (PVDF) membrane. The modification buffer used in Example 1 was added thereto, and incubation was carried out at 37° C. for 2.5 hours in a light-shielded vessel to modify citrulline residues.

The resultant was washed with PBS containing 0.05% Tween 20 and blocked with TBS containing 5% skimmed milk. The AMC antibody diluted 3,200-fold with the blocking solution was added, the resultant was incubated at 4° C. overnight. After washing, incubation was carried out at room temperature for an additional 1 hour with the use of HRP-conjugated goat anti-rabbit IgG (H+L) (Bio-Rad) diluted 1:5000-fold in the blocking solution as a secondary antibody.

As a result, the citrullinated protein was detected in the serum 14 days after injection of pGPI, as shown in FIG. 5A, although no citrullinated protein was detected in the control mice. The citrullinated protein band was detected as a single band of approximately 120 kD. The protein level significantly increased 14 days after immunization compared to the control mice, and then decreased in the serum 28 days after immunization in correlation with healing of arthritis. The 120-kD band intensity in each lane was analyzed via densitometry using the ImageQuant LAS-4000 densitometer (GE Healthcare). The results of analysis (FIG. 5B) were found to be consistent with the phenomenon demonstrated in Reference Example 1 (FIG. 2A).

The results of measurement performed in Example 1 demonstrate the presence of the anti-CCP antibody detected in the serum from 14 days after injection of pGPI and indirectly indicate the presence of the citrullinated protein as the antigen. In this example, however, the citrullinated protein was not detected via Western blot analysis when the citrulline residue was not modified. This indicates that the citrulline-specific band intensity may reflect the disease state.

Example 4: Detection of Citrullinated Protein in Serum of pGIA Mice 2

Western blot analysis was performed in the same manner as in Example 3 using the serum samples of the control mice (CFA) and the pGIA mice (pGPI) obtained 14 days after injection of CFA or pGPI. As a result, no citrullinated protein was detected in the samples obtained from the control mice but a clear band of the citrullinated protein was detected at a position of approximately 120 kD in the samples obtained from the pGIA mice, as shown in FIG. 6A. Significantly strong band intensity was also observed in the samples obtained from the pGIA mice as a result of densitometry (FIG. 6B).

Example 5: Identification of Citrullinated Protein in Serum of pGIA Mice 1

Figure 7:
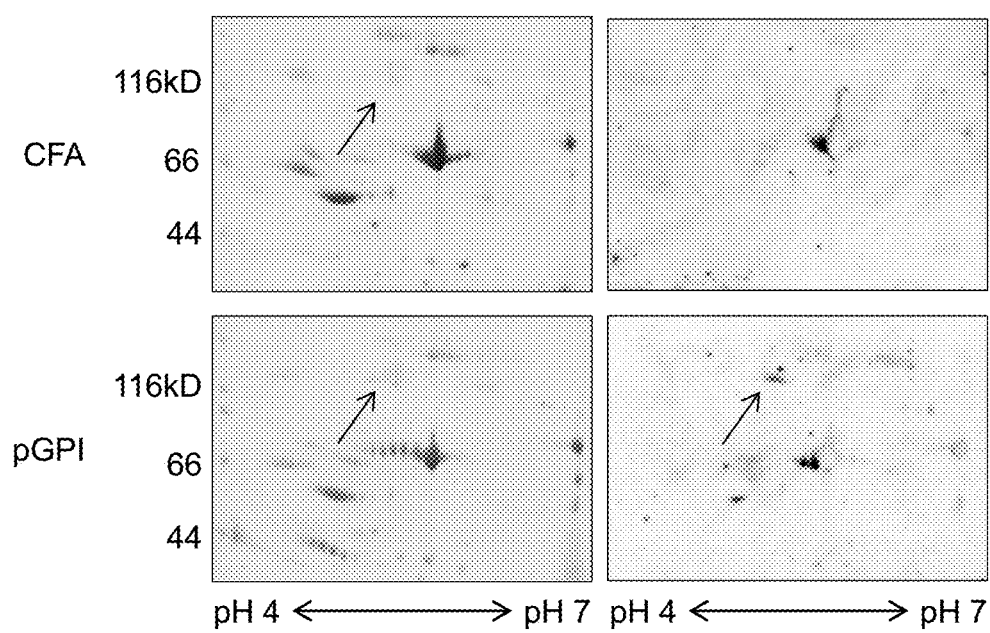
FIG. 7A shows the results of analysis performed by developing the serum samples obtained from pGIA mice (pGPI) and control mice (CFA) 14 days after immunization via 2D-PAGE, staining the serum samples with Coomassie brilliant blue, and subjecting the resultants to Western blot analysis using the AMC antibody. While a citrullinated protein was detected at a position of approximately 120 kD and pH 5.3 in the serum samples from the pGIA mice, it was not detected in the serum samples from the control mice.
FIG. 7B shows a list of candidate proteins that can be present at a position of approximately 120 kD and pH 5.3 in the serum of the pGIA mice and the control mice. ITIH4 is most likely to be present at the position indicated above.

The serum samples (100 μg) obtained from mice into which CFA or pGPI had been injected were developed by two-dimensional (2D)-PAGE, the gel was subjected to Coomassie brilliant blue staining using the GelCode Blue Stain Reagent (Thermo Fisher Scientific), and Western blot analysis was performed with the use of the AMC antibody in the same manner as in Example 3. As a result, a citrullinated protein spot was detected at a position of approximately 120 kD and pH 5.3 in the serum samples obtained from the pGIA mice (FIG. 7A). This citrullinated protein spot was cleaved from the gel.

The gel section was incubated at 37° C. overnight together with a MS-grade modified trypsin (6.7 ng/μl; Promega) and digested. The peptide obtained was analyzed using the BEH130 nanoAcquity C18 column (100-mm×75 μm, 1.7 μm) held at 35° C. and the nanoAcquity Ultra-performance LC (UPLC) system (Waters Co.). The conditions for analysis are shown below.

Mobile phase A: 0.1% (v/v) formic acid and water
Mobile phase B: 0.1% (v/v) formic acid and acetonitrile
Gradient: 3% B for 1 min
  3% to 40% B in 77 min
  40% B for 3 min
  40% to 95% B in 1 min
  95% for 4 min
  95% to 3% B in 10 min
Flow rate: 0.3 μl/min Subsequently, the eluted peptide was analyzed using a Q-TOF mass spectrometer (Synapt high definition mass spectrometry system, Waters) and Waters MassLynx software (version 4.1) (capillary voltage: 3.5 kV; cone voltage: 40 V; electrospray ionization mode). With the aid of low (6 eV) or gradually elevating (25 to 40 eV) collision energy, intact precursor ions and product ions were detected (ion source temperature: 100° C.; detected at a cationic mode). The m/z 50 to 1990 data were obtained and referred to the databases.

As a result of analysis, regardless of citrullination, 4 types of protein species existing in an amount exceeding 10%; i.e., inter-α-trypsin inhibitor heavy chain 4 (O54882, ITIH4); ceruloplasmin (E9PZD8); inter-α-trypsin inhibitor heavy chain 3 (Q61704, ITIH3); and glycosylphosphatidylinositol-specific phospholipase D (Q7TNZ4), were identified (FIG. 7B).

On the basis of the proportion of the content thereof (i.e., the coverage), the inter-α-trypsin inhibitor heavy chain 3 (ITIH3) and the inter-α-trypsin inhibitor heavy chain 4 (ITIH4) were selected as candidate proteins, and citrullination thereof was examined via nanoUPLC-MS$^E$.

Figure 8:
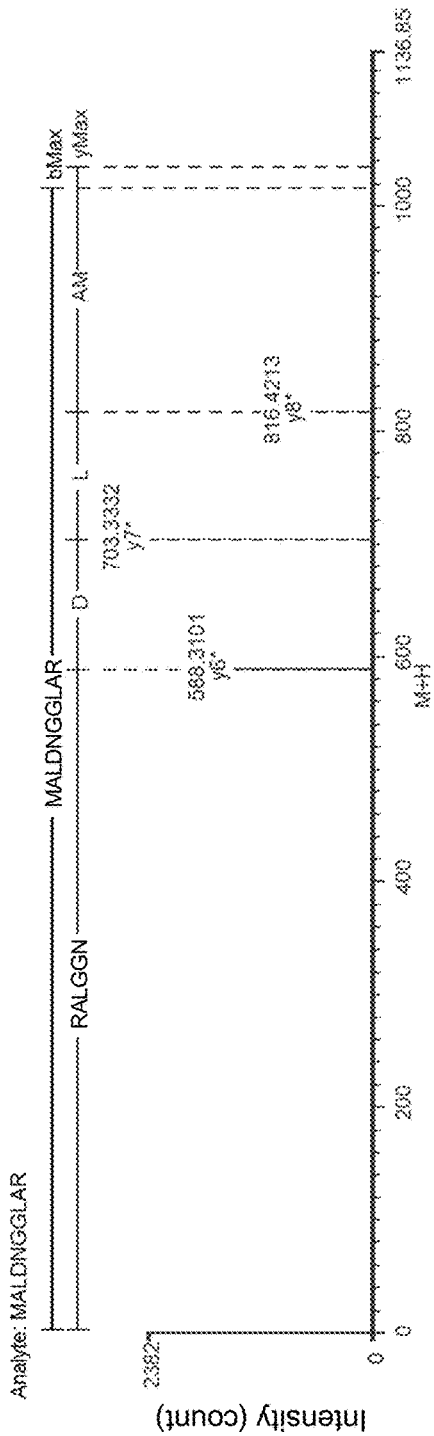
FIG. 8A shows ITIH4429-438 (SEQ ID NO: 3) and the MS spectrum of a modified peptide having citrullinated arginine (R438) in the pGIA sample (SEQ ID NO: 4).
FIG. 8B shows the MS and $MS^E$ data of the pGIA sample. Citrullinated residue was identified by modified y6, y7, and y8 ions.

FIG. 8 shows the results of mass spectrometry of the peptide derived from mouse ITIH4. Mouse ITIH4 has the amino acid sequence as shown in SEQ ID NO: 1, and the peptide represented by SEQ ID NO: 3 consisting of 10 amino acids corresponding to amino acids 429 to 438 in the amino acid sequence as shown in SEQ ID NO: 1 (i.e., MALDNGGLAR (ITIH4429-438)) was found to be modified at its C terminus; i.e., arginine 438 in SEQ ID NO: 1 had been citrullinated (the peptide represented by SEQ ID NO: 4). Specifically, ITIH4 comprising citrullinated R438 was identified as a significantly citrullinated protein in the serum samples obtained from the pGIA mice (FIG. 8A and FIG. 8B), and citrullination at this position was found to be pGIA-specific.

Example 6: Identification of Citrullinated Protein in Serum of pGIA Mice 2

The serum samples obtained from the pGIA mice and the control mice 14 days after injection were separated via SDS-PAGE, stained with Coomassie brilliant blue (FIG. 9A), and subjected to Western blot analysis using the AMC antibody (FIG. 9B). As a result, a citrullinated protein was detected at a position of approximately 120 kD in the serum samples obtained from the pGIA mice but was not detected in the serum samples obtained from the control mice, similarly as Example 5.

This citrullinated protein spot was cleaved from the gel and analyzed via nanoUPLC-MS and nanoUPLC-MS$^E$. As a result, the peptide (SEQ ID NO: 4) derived from the peptide represented by SEQ ID NO: 3 (ITIH4429-438) by citrullination of arginine at the C terminus was detected (data not shown), similarly as Example 5.

Example 7: Detection of Citrullinated Protein in Serum Samples Derived from Human RA Patients Serum samples were collected from 63 patients diagnosed to have rheumatoid arthritis in accordance with the 1987 American College of Rheumatology (ACR) guidelines and 22 healthy subjects, and subjected to Western blot analysis in the same manner as in Example 3.

As a result, citrullinated protein bands as observed in the samples from mice were specifically detected at a position of approximately 120 kD in the serum samples from some RA patients, but no bands were detected in the serum samples from healthy subjects (FIG. 10A). The 120 kD band intensity in each lane was analyzed via densitometry. As a result, the band of interest was found to be RA patient-specific (FIG. 10B). The results demonstrate that a citrullinated protein of approximately 120 kD increases in the serum of RA patients and such increase may be correlated with arthritis.

Figure 11:
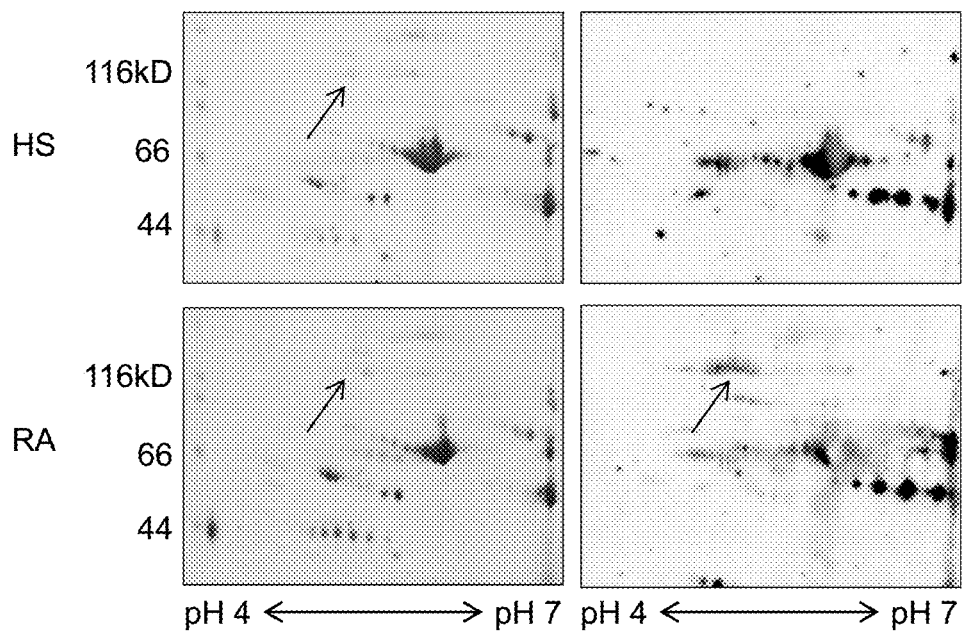
FIG. 11A shows the results of analysis performed by developing the serum samples obtained from patients with rheumatoid arthritis (RA) and healthy subjects (HS) via 2D-PAGE, staining the serum samples with Coomassie brilliant blue, and subjecting the resultants to Western blot analysis using the AMC antibody. While a citrullinated protein was detected at a position of approximately 120 kD and pH 5.3 in the serum samples from patients with rheumatoid arthritis, it was not detected in the serum samples from healthy subjects.
FIG. 11B shows a list of candidate proteins that can be present at a position of approximately 120 kD and pH 5.3 in the serum of patients with rheumatoid arthritis and healthy subjects. ITIH4 is most likely to be present at the position indicated above.

Example 8: Identification of Citrullinated Protein in Serum Samples from RA Patients In the same manner as in Example 5, serum samples obtained from human RA patients were subjected to 2D-PAGE and Western blot analysis, and a citrullinated protein spot was detected at a position of approximately 120 kD and pH 5.3 as with the case of the mice (FIG. 11A). After Coomassie brilliant blue staining, the protein spot was cleaved from the gel and subjected to nanoUPLC-MS. Regardless of the occurrence of citrullination, 3 types of protein species existing in an amount exceeding 10%; i.e., the inter-α-trypsin inhibitor heavy chains 4 (B7Z545 and B2RMS9, ITIH4); complement C3 (P01024); and ceruloplasmin (A5PL27), were identified (FIG. 11B). As with the case of the mice, ITIH4 was identified at the highest proportion, suggesting that ITIH4 is most likely to be the citrullinated protein.

Figure 12:
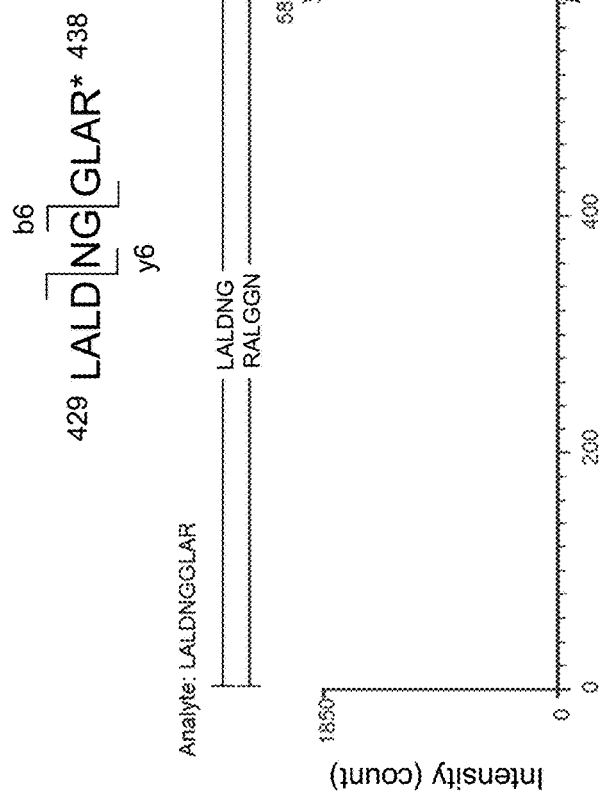
FIG. 12A shows ITIH4429-438 (SEQ ID NO: 7) and the MS spectrum of a modified peptide having citrullinated arginine (R438) in the samples from patients with rheumatoid arthritis (SEQ ID NO: 8).
FIG. 12B shows the MS and $MS^E$ data of the samples from patients with rheumatoid arthritis. Citrullinated residue was identified by an unmodified b6 ion and a modified y6 ion.

FIG. 12 shows the results of mass spectrometry of the peptide derived from human ITIH4 via nanoUPLC-MS$^E$. Human ITIH4 has the amino acid sequence as shown in SEQ ID NO: 5, and the peptide represented by SEQ ID NO: 7 consisting of 10 amino acids corresponding to amino acids 429 to 438 in the amino acid sequence as shown in SEQ ID NO: 5 (i.e., LALDNGGLAR (ITIH4429-438)) was found to be modified at its C terminus; i.e., arginine 438 in SEQ ID NO: 5 had been citrullinated (the peptide represented by SEQ ID NO: 8). Specifically, ITIH4 comprising citrullinated R438 was identified as a significantly citrullinated protein in the serum of RA patients, as with the case of the mice (FIG. 12A and FIG. 12B), citrullination at this position was found to be RA patient-specific, and such citrullination was not detected in the samples from healthy subjects.

Example 9: Correlation with Clinical Features

In some patients, ITIH4 citrullination was not detected via Western blot analysis performed in Example 7. Thus, 60 RA patients whose detailed data had been obtained were divided into two groups; i.e., the patient group in which citrullinated ITIH4 was detected in the serum (+) and the patient group in which citrullinated ITIH4 was not detected (−), using the cut-off value of 0.46 equivalent to the band intensity for healthy subjects ±3SD, and various clinical features of both groups were compared. The results are shown in Table 1.

TABLE 1

|  | Total | Citrullinated ITIH4 | | p value |
|---|---|---|---|---|
|  |  | + | − |  |
| n (%) | 60 | 49 (82%) | 11 (18%) |  |
| Age | 52.2 ± 1.9 | 51.3 ± 2.2 | 55.9 ± 3.9 | 0.355 |
| Female, n (%) | 48 (80%) | 38 (78%) | 10 (91%) | 0.317 |
| DAS28-CRP | 3.9 ± 0.2 | 4.1 ± 0.2 | 3.3 ± 0.4 | 0.040 * |
| CRP (mg/dl) | 2.18 ± 0.30 | 2.46 ± 0.34 | 0.93 ± 0.56 | 0.047 * |
| Anti-CCP antibody (U/ml) | 131.6 ± 21.6 | 138.9 ± 24.6 | 93.4 ± 39.0 | 0.462 |
| Positive, n (%) | 46 (82%) | 39 (83%) | 7 (78%) | 0.709 |
| RF (U/ml) | 210.6 ± 46.1 | 242.3 ± 55.0 | 69.5 ± 35.5 | 0.011 * |
| MMP-3 (ng/ml) | 198.5 ± 21.8 | 214.7 ± 25.7 | 127.9 ± 20.1 | 0.122 |
| Stage (I/II/III/IV) | 17/18/8/15 | 14/15/5/13 | 3/3/3/2 | 0.662 |
| Use of prednisolone, n (%, average dose (mg/day)) | 51 (85%, 6.9) | 41 (84%, 7.1) | 10 (91%, 6.4) | 0.544 |
| Use of methotrexate, n (%, average dose (mg/week)) | 40 (67%, 10.1) | 31 (63%, 10.1) | 10 (91%, 10.0) | 0.075 |

DAS28: disease activity score at 28 joints; CRP: C-reactive protein; CCP: cyclic citrullinated peptide; RF: rheumatoid factor; MMP-3: matrix metalloproteinase-3
Numerical values represent mean ± SEM.

As shown in Table 1, the DAS28-CRP scores (p=0.040), the rheumatoid factor (RF, p=0.011) level, and the C-reactive protein (CRP, p=0.047) level of the group of patients with citrullinated ITIH4 in the serum were found to be significantly higher than those of the group of RA patients without citrullinated ITIH4 in the serum. In contrast, no difference was observed between groups in terms of anti-CCP antibody levels.

The correlation between the results of citrullinated ITIH4 detection and the serum reactions of the rheumatoid factor (RF) and of the anti-CCP antibody (ACPA) was examined. As a result, 7 patients (88%) among 8 RA patients having negative serum reactions for both ACPA and RF were found to show positive serum reactions to citrullinated ITIH4, as shown in Table 2. The results indicate that citrullinated ITIH4 may be correlated with disease activity and local inflammation at the joint. In addition, patients who were found to show negative serum reactions in a conventional technique using RF and ACPA may yield positive results. Thus, citrullinated ITIH4 can serve as a marker for assistance for RA diagnosis. In addition, the results of ITIH4 detection were found to reflect the disease activity more precisely, compared with the results of ACPA detection.

TABLE 2

|  | RF(+) ACPA(+) | RF(+) ACPA(−) | RF(−) ACPA(+) | RF(−) ACPA(−) |
| --- | --- | --- | --- | --- |
| n | 42 | 2 | 4 | 8 |
| cit-ITIH4 positive, n (%) | 38 (91%) | 1 (50%) | 1 (25%) | 7 (88%) |
| cit-ITIH4 titer | 2.2 ± 0.5 | 1.3 ± 0.9 | 0.6 ± 0.3 | 0.9 ± 0.3 |

Example 10: Verification of RA-Specific Citrullination 1

Serum samples were collected from 60 patients with rheumatoid arthritis (RA), 30 healthy subjects (HS), 12 patients with osteoarthritis (OA), 15 patients with systemic lupus erythematodes (SLE), and 27 patients with Sjogren's syndrome (SS), and expression of the citrullinated protein of approximately 120 kD was analyzed via Western blot analysis using the AMC antibody. The SLE patients and the SS patients mentioned above do not have complications of rheumatoid arthritis.

Figure 14:
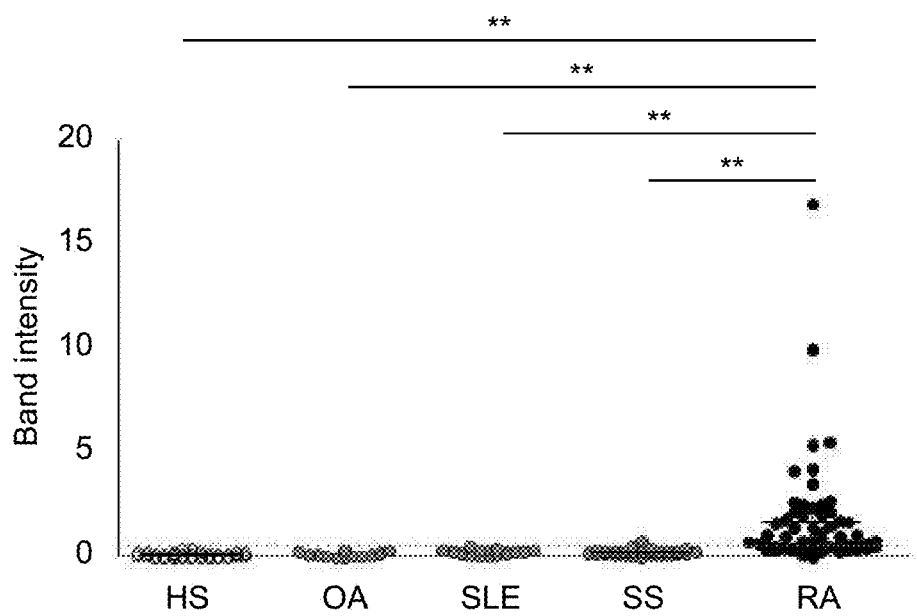
FIG. 14 shows the 120 kD citrullinated protein band intensity detected by subjecting the serum samples obtained from healthy subjects (HS, n=30), patients with osteoarthritis (OA, n=12), patients with systemic lupus erythematodes (SLE, n=15), patients with Sjogren's syndrome (SS, n=27), and patients with rheumatoid arthritis (RA, n=60) to Western blot analysis using the AMC antibody. Each dot indicates the result concerning one sample, a horizontal bar indicates a mean, a vertical bar indicates SEM, and a dot line indicates a cut-off value. **: $p<0.01$.

As a result, a clear band of a citrullinated protein was detected at a position of approximately 120 kD in the serum samples obtained from RA patients, but no band was detected in the serum samples obtained from patients with other diseases, as shown in FIGS. 13A to 13D. In addition, expression of the citrullinated protein at a position of approximately 120 kD was found to be RA patient-specific on the basis of the results shown in FIG. 14, which shows a chart representing the band intensity detected at a position of approximately 120 kD via Western blot analysis performed on each patient.

The subjects were evaluated as to positivity/negativity using the band intensity of mean±3SD for healthy subjects (HS) as the cut-off value. As a result, 49 patients among 60 patients with rheumatoid arthritis (RA) were evaluated positive but only 3 patients among 84 patients with diseases other than RA were evaluated positive (Table 3). The results demonstrate that sensitivity of RA diagnosis by the method according to the present invention was found to be 81.7% and specificity thereof was found to be 96.4%.

TABLE 3

|  | RA patients | Non-RA patients |
| --- | --- | --- |
| cit-ITIH4 positive | 49 | 3 |
| cit-ITIH4 negative | 11 | 81 |

FIG. 13E shows the results of Western blot analysis of the serum samples obtained from healthy subjects (HS), patients with Sjogren's syndrome (SS), and patients with rheumatoid arthritis (RA) performed with the use of the anti-ITIH4 antibody (left) and the AMC antibody (right). The results of analysis demonstrate the presence of citrullinated ITIH4 at a position of approximately 120 kD in the serum samples obtained from RA patients. While the ITIH4 protein was detected in samples obtained from healthy subjects and SS patients, the ITIH4 protein was not citrullinated.

The results demonstrate that citrullination of the ITIH4 protein is specific to rheumatoid arthritis.

Example 11: Verification of RA-Specific Citrullination 2

On the basis of the results of the detection performed in Example 10 that had detected the presence of a considerable amount of noncitrullinated ITIH4 in healthy subjects, the total ITIH4 level in the serum samples obtained from healthy subjects and RA patients were measured with the use of the ITIH4 quantification ELISA kit (Catalog No. DY8157-05, R&D Systems).

Figure 15:
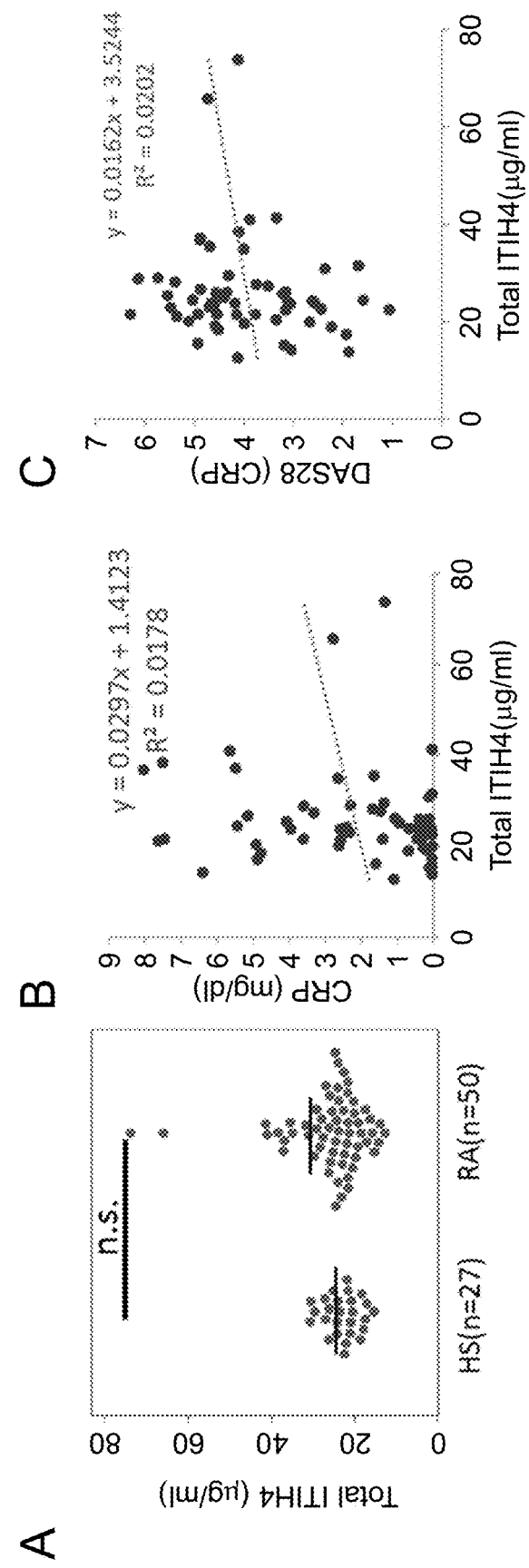
FIG. 15A shows protein concentration detected via ELISA analysis using the ITIH4 quantification ELISA kit (R&D Systems) for the serum samples obtained from healthy subjects (HS, n=27) and patients with rheumatoid arthritis (RA, n=50). Each dot indicates the result concerning one sample, a horizontal bar indicates a mean, and "n.s." indicates that there is no significant difference.
FIG. 15B shows the correlation between the total ITIH4 level and the CRP level in the serum samples obtained from patients with rheumatoid arthritis (RA). Each dot indicates the result concerning one sample.
FIG. 15C shows the correlation between the total ITIH4 level and the DAS28 (CRP) level in the serum samples obtained from patients with rheumatoid arthritis (RA). Each dot indicates the result concerning one sample.

As a result, no significant difference was observed between healthy subjects and RA patients in terms of the total ITIH4 level, regardless of occurrence of citrullination, as shown in FIG. 15A.

In addition, the samples obtained from healthy subjects and RA patients were analyzed in terms of the correlation between the total ITIH4 level and the CRP level (FIG. 15B) and the DAS28 (CRP) score (FIG. 15C) in the serum. As a result, no correlation was observed.

The results demonstrate that the total ITIH4 protein level would not specifically elevate in RA patients and that the total ITIH4 protein level would not serve as a marker associated with arthritis.

Example 12: Correlation with Disease Activity Index

Whether or not the citrullinated ITIH4 level in RA patients would be correlated with the known composite disease activity index was examined.

To date, DAS28-CRP, DAS28-ESR, Simplified Disease Activity Index (SDAI), Clinical Disease Activity Index (CDAI), and the like have been known as the disease activity indices for rheumatoid arthritis. Such indices are the composite disease activity indices calcurated based on pressure pain and swelling at 28 joints, overall evaluation of a patient, overall evaluation made by a doctor, CRP level, and other factors in combination.

Figure 16:
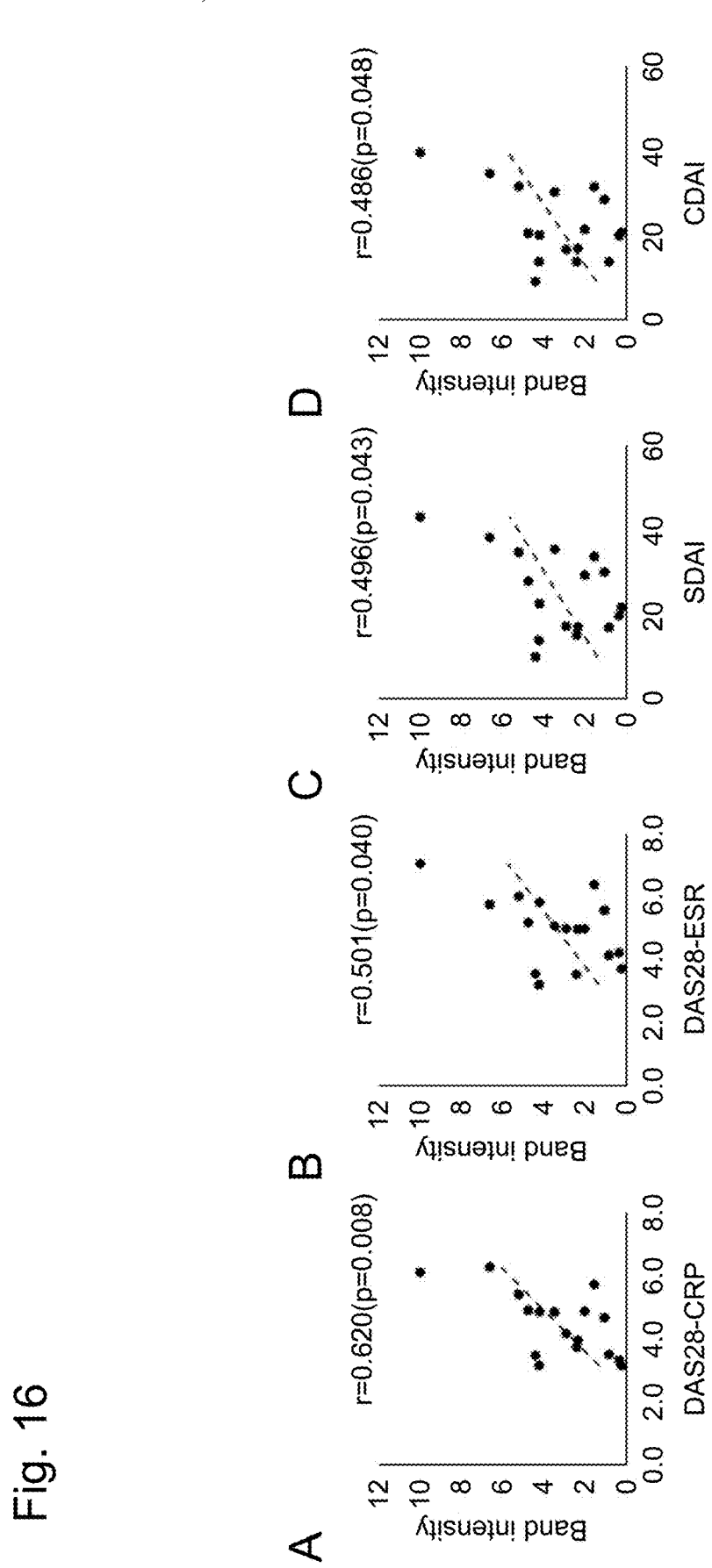
FIG. 16 shows the correlation between the citrullinated ITIH4 levels in the serum samples obtained from patients with rheumatoid arthritis (RA, n=17) before treatment and the disease activity index scores (A: DAS28-CRP; B: DAS28-ESR; C: SDAI; D: CDAI). Each dot indicates the result concerning one sample. r: correlation coefficient.

The correlation between the citrullinated ITIH4 levels in the serum samples obtained from 17 RA patients before treatment (i.e., the intensity of a band of approximately 120 kD determined with the use of the AMC antibody) and the disease activity indices was examined. As a result, the citrullinated ITIH4 level was found to be correlated with any of the indices, as shown in FIG. 16.

Example 13: Correlation with Symptoms Alleviated by a Therapeutic Agent for Rheumatoid Arthritis From the 17 citrullinated ITIH4-positive RA patients who had been examined in terms of the correlation with the disease activity indices in Example 12, serum samples were collected before treatment with abatacept (n=8) or infliximab (n=9) and after treatment over a period of 24 weeks, changes in the citrullinated ITIH4 level and in the disease activity index were examined before and after the treatment, and the correlation therebetween was then examined.

As a result, the citrullinated ITIH4 levels in the serum samples obtained from patients were found to have apparently decreased via treatment with abatacept (lanes 1 and 2) and infliximab (lanes 3 to 8), as shown in FIG. 17A. This indicates that the citrullinated ITIH4 level in the serum decreases as the symptoms are alleviated by treatment, regardless of the action mechanism of the therapeutic agent.

FIG. 17B and FIG. 17C each demonstrate a positive correlation between lowering of the citrullinated ITIH4 level in the serum and lowering of the disease activity indices (DAS28-CRP and DAS28-ESR) calculated before and after treatment.

On the basis of the results demonstrated above, citrullinated ITIH4 was verified to serve as a novel serum marker that reflects the disease activity of an RA patient.

Example 14: Verification of Antigenicity of Citrullinated ITIH4 Peptide

Peptides each consisting of 20 amino acids including amino acid 438 in the amino acid sequence of the human ITIH4 protein as shown in SEQ ID NO: 5 and that as shown in SEQ ID NO: 6; i.e., the ITIH4$_{428-447}$ peptide comprising arginine at position 438 (native-pITIH4) and the ITIH4$_{428-447}$ peptide comprising citrulline at position 438 (cit-pITIH4), were synthesized (peptides were synthesized by Scrum Inc., purity: 95%). The antibody reaction of the serum samples obtained from RA patients to the peptides above was evaluated.

A 96-well plate (Nunc, MaxiSorp) was coated with either of the peptides at 10 µg/ml at 4° C. over a period of 12 hours, the plate was washed and blocked, 1:200 diluted serum samples obtained from RA patients (n=60) and healthy subjects (n=30) were introduced into PBS containing 1% bovine serum albumin (BSA), and the resultant was allowed to stand at room temperature for 2 hours. After washing, 1:10000 diluted HRP-conjugated goat anti-human IgG (H+L)(Abcam) was added, and the resultant was allowed to stand at room temperature for 1 hour. After washing, TMB microwell peroxidase substrate (KPL) was added to develop color, and the optical density at 450 nm was measured using a microplate reader.

Figure 18:
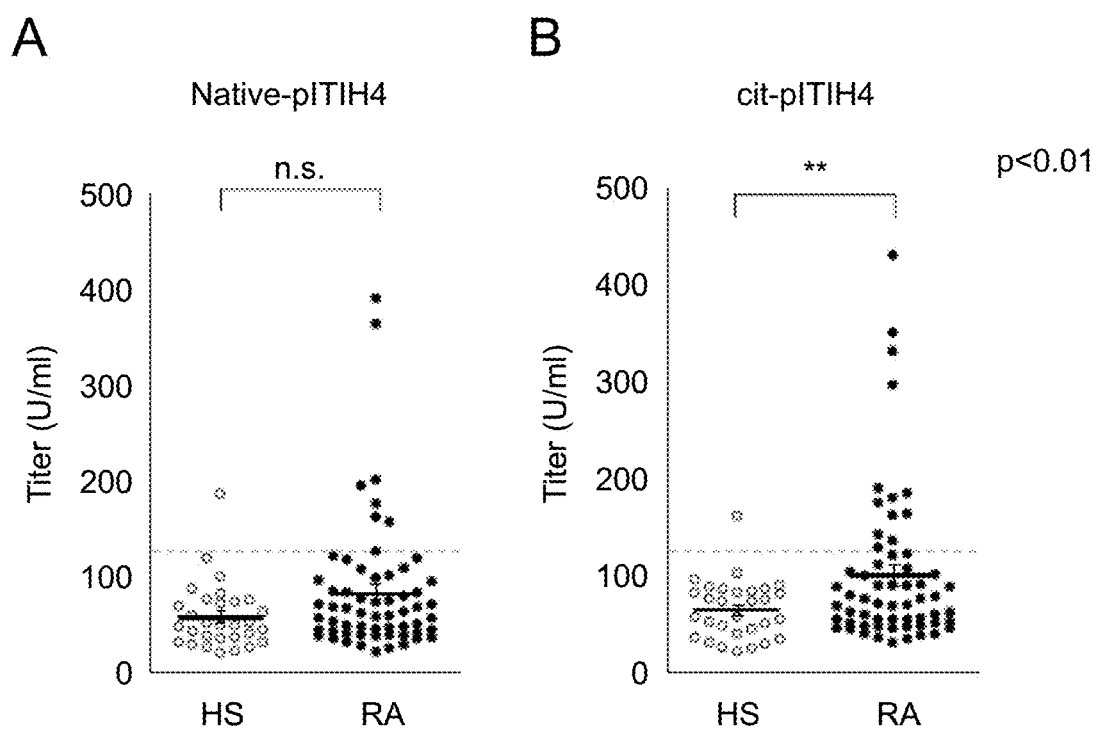
FIG. 18 shows the results of the antibody reaction of the serum samples obtained from healthy subjects (HS, n=30) and patients with rheumatoid arthritis (RA, n=60) against the noncitrullinated ITIH4 428-447 peptide (native-pITIH4) or the citrullinated ITIH4 428-447 peptide (cit-pITIH4) detected via ELISA. Each dot indicates the result concerning one sample, a horizontal bar indicates a mean, a vertical bar indicates SEM, and a dot line indicates a cut-off value. **: $p<0.01$, n.s.: not significant.

FIG. 18A shows the antibody titer against the noncitrullinated ITIH4 peptide (native-pITIH4) in serum samples obtained from healthy subjects and RA patients and demonstrates that there is no significant difference between healthy subjects and RA patients in terms of antibody responses. FIG. 18B shows the antibody titer against the citrullinated ITIH4 peptide (cit-pITIH4) and demonstrates that the antibody levels of RA patients are significantly higher than those of healthy subjects. The cut-off value of mean±2SD for healthy subjects was used.

INDUSTRIAL APPLICABILITY

ACPA that is currently used is intended to detect the presence of the anti-CCP antibody in the blood. The antibody titer that has once elevated does not lower even if remission is achieved by treatment, and it is not correlated with disease activity. CRP and other indices are nonspecifically increased due to infectious diseases and other causes and specificity thereof is accordingly low. While DAS28 serving as the composite index for RA yields highly reliable results, it involves many parameters to obtain numerical values. Thus, such technique cannot lead to results rapidly.

The method according to the present invention that detects citrullination of ITIH4 enables RA-specific detection. Further, citrullination of ITIH4 is highly correlated with disease activity, it can be used for monitoring the disease, and it can be a very effective biomarker in the clinical setting. According to the present invention, in addition, a novel therapeutic target for RA is identified. Accordingly, a novel therapeutic agent for alleviating clinical symptoms of RA may be provided.

All publications, patents, and patent applications cited herein are incorporated herein by reference in their entirety.

The invention claimed is:

1. A method for detecting a citrullinated protein in a subject, comprising:
   separating or concentrating a fraction comprising inter-α-trypsin inhibitor heavy chain (ITIH) 4 from a biological sample from the subject; and
   detecting the presence or the amount of citrullination of an arginine residue of the (ITIH) 4 in the fraction.

2. A method for determining disease activity of rheumatoid arthritis in a subject and/or therapeutic effects of an agent for rheumatoid arthritis, comprising:
   conducting the method according to claim 1 before and after administering the agent, and
   comparing the amount of the citrullinated protein before and after administering the agent, wherein an increased amount of the citrullinated protein indicates a more advanced disease state, and wherein a decreased amount of the citrullinated protein indicates alleviation of the disease.

3. The method according to claim 1, wherein the arginine residue is an arginine residue at position 438 in the amino acid sequence as shown in SEQ ID NO: 1 or 5.

4. The method according to claim 1, wherein the biological sample is a whole blood, plasma, serum, skin, or joint tissue sampled from the subject.

5. The method according to claim 1, wherein the citrullination is detected by mass spectrometry, Western blot analysis, immunohistological detection, immunoprecipitation, or ELISA.

6. A method for diagnosis of rheumatoid arthritis or a method for assisting diagnosis of rheumatoid arthritis in a subject, comprising:
   separating or concentration a fraction comprising inter-a-trypsin inhibitor heavy chain (ITIH) 4 from a biological sample from the subject;
   detecting the amount of citrullination of an arginine residue of the ITIH4 in the fraction, and
   comparing the amount of citrullinated ITIH4 in the fraction with that detected for a healthy subject or a reference value,
   wherein an increased amount of citrullinated ITIH4 indicates that the subject has rheumatoid arthritis.

7. The method according to claim 1, further comprising collecting the biological sample from the subject.

8. The method according to claim 6, further comprising collecting the biological sample from the subject.

9. The method according to claim 6, wherein the arginine residue is an arginine residue at position 438 in the amino acid sequence as shown in SEQ ID NO: 1 or 5.

10. The method according to claim 6, wherein the biological sample is a whole blood, plasma, serum, skin, or joint tissue sampled from the subject.

11. The method according to claim 6, wherein the citrullination is detected by mass spectrometry, Western blot analysis, immunohistological detection, immunoprecipitation, or ELISA.

* * * * *